United States Patent
Diaz et al.

(10) Patent No.: US 9,814,842 B2
(45) Date of Patent: Nov. 14, 2017

(54) SAFETY SYRINGE

(71) Applicant: Credence Medsystems Inc., Menlo Park, CA (US)

(72) Inventors: Stephen H. Diaz, Palo Alto, CA (US); John F. Shanley, Emerald Hills, CA (US); Alan E. Shluzas, San Carlos, CA (US); Jeff Tillack, Foster City, CA (US); Dan Thayer, Tustin, CA (US)

(73) Assignee: Credence MedSystems, Inc., Menlo Park, CA (US)

( * ) Notice: Subject to any disclaimer, the term of this patent is extended or adjusted under 35 U.S.C. 154(b) by 649 days.

(21) Appl. No.: 14/321,706

(22) Filed: Jul. 1, 2014

(65) Prior Publication Data

US 2015/0005706 A1 Jan. 1, 2015

Related U.S. Application Data

(60) Provisional application No. 61/841,702, filed on Jul. 1, 2013.

(51) Int. Cl.
*A61M 5/32* (2006.01)
*A61M 5/315* (2006.01)

(52) U.S. Cl.
CPC ...... *A61M 5/3232* (2013.01); *A61M 5/31501* (2013.01); *A61M 5/31505* (2013.01);
(Continued)

(58) Field of Classification Search
CPC . A61M 5/3232; A61M 5/3234; A61M 5/3224
See application file for complete search history.

(56) References Cited

U.S. PATENT DOCUMENTS 4,874,381 A 10/1989 Vetter
4,927,414 A 5/1990 Kulli
(Continued)

FOREIGN PATENT DOCUMENTS

EP 2022521 A1 2/2009
KR 20130000843 U 2/2013
(Continued)

OTHER PUBLICATIONS

International Search Report and Written Opinion dated Jan. 6, 2015, International Patent Application No. PCT/US14/45160 with International Filing Date of Jul. 1, 2014, (14 pages).
(Continued)

*Primary Examiner* — Laura Bouchelle
(74) *Attorney, Agent, or Firm* — Vista IP Law Group, LLP

(57) ABSTRACT

One embodiment is directed to a safety syringe system, comprising a syringe body; a plunger tip positioned within the syringe body; a needle assembly removably coupleable to the distal end of the syringe body such that a medicinal fluid may be transferred through a retractable needle coupled to a needle housing comprising the needle assembly upon insertion of the plunger tip relative to the syringe body; and a plunger control assembly coupled to the plunger tip and configured to facilitate manual insertion of the plunger tip relative to the syringe body; wherein upon insertion and release of the plunger tip, a retraction load coupled between the syringe body and the plunger tip causes the plunger tip to be proximally withdrawn, pulling the retractable needle proximally relative to the needle housing to a safe locked and retracted state.

19 Claims, 44 Drawing Sheets

(52) U.S. Cl.
CPC ........ *A61M 5/3202* (2013.01); *A61M 5/3221* (2013.01); *A61M 5/3234* (2013.01); *A61M 2005/31508* (2013.01); *A61M 2005/323* (2013.01); *A61M 2005/3223* (2013.01); *A61M 2005/3224* (2013.01); *A61M 2005/3231* (2013.01); *A61M 2005/3242* (2013.01)

(56) References Cited

U.S. PATENT DOCUMENTS

| | | | |
|---|---|---|---|
| 5,002,536 A | | 3/1991 | Thompson et al. |
| 5,053,010 A | * | 10/1991 | McGary .............. A61M 5/3234 604/110 |
| 5,112,316 A | | 5/1992 | Venturini |
| 5,211,628 A | | 5/1993 | Marshall |
| 5,215,533 A | | 6/1993 | Robb |
| 5,330,430 A | | 7/1994 | Sullivan |
| 5,342,310 A | * | 8/1994 | Ueyama .............. A61M 5/3234 604/110 |
| 5,403,288 A | | 4/1995 | Stanners |
| 5,615,772 A | * | 4/1997 | Naganuma ............ A61M 5/002 206/364 |
| 5,669,887 A | | 9/1997 | Cooper |
| 5,676,346 A | | 10/1997 | Leinsing |
| 5,681,292 A | | 10/1997 | Tober et al. |
| 5,792,107 A | * | 8/1998 | Petrocelli ............ A61M 5/3234 604/110 |
| 5,993,418 A | * | 11/1999 | Alexander .............. A61M 5/32 604/110 |
| 6,010,486 A | | 1/2000 | Carter et al. |
| 6,090,081 A | | 7/2000 | Sudo et al. |
| 6,183,440 B1 | | 2/2001 | Bell |
| 6,413,237 B1 | | 7/2002 | Caizza et al. |
| 6,585,700 B1 | | 7/2003 | Trocki et al. |
| 6,706,019 B1 | | 3/2004 | Parker et al. |
| 7,500,964 B2 | | 3/2009 | Shaw et al. |
| 8,088,104 B2 | * | 1/2012 | Smith ................. A61M 5/3234 604/110 |
| 8,167,837 B2 | * | 5/2012 | Judd ................... A61M 5/3234 604/110 |
| 2003/0004468 A1 | | 1/2003 | Righi et al. |
| 2006/0253074 A1 | * | 11/2006 | Thayer ................ A61M 5/3234 604/110 |
| 2006/0258984 A1 | | 11/2006 | Kiehne |
| 2007/0129675 A1 | | 6/2007 | Summerville et al. |
| 2008/0027381 A1 | | 1/2008 | Smith et al. |
| 2008/0269690 A1 | | 10/2008 | Felix-Faure |
| 2009/0018503 A1 | | 1/2009 | Walton et al. |
| 2010/0010450 A1 | | 1/2010 | Runfola et al. |
| 2010/0262119 A1 | | 10/2010 | Schraga |
| 2010/0286609 A1 | | 11/2010 | Mahurkar |
| 2013/0030382 A1 | | 1/2013 | Sudo |
| 2013/0079716 A1 | | 3/2013 | Thorley et al. |
| 2015/0073344 A1 | | 3/2015 | Van Damme et al. |

FOREIGN PATENT DOCUMENTS

| | | |
|---|---|---|
| WO | WO 03/039634 A1 | 5/2003 |
| WO | WO 2005058398 A1 | 6/2005 |
| WO | WO 2005058399 A1 | 6/2005 |
| WO | 2010/065375 A1 | 6/2010 |
| WO | 2012/038959 A2 | 3/2012 |
| WO | WO 2012/073035 A1 | 6/2012 |
| WO | WO 2012151314 A2 | 8/2012 |

OTHER PUBLICATIONS

Non-Final Office Action dated May 3, 2017 for U.S. Appl. No. 14/321,735.
European Extended Search Report dated Feb. 21, 2017 for EP Appln. No. 14819246.1.
Non-Final Office Action dated May 26, 2017 for U.S. Appl. No. 14/321,729.
Non-Final Office Action dated May 30, 2017 for U.S. Appl. No. 14/321,721.
Non-Final Office Action dated Jul. 18, 2017 for U.S. Appl. No. 14/321,713.
International Search Report and Written Opinion dated Apr. 8, 2015, International Patent Application No. PCT/US14/65998 with International Filing Date of Nov. 17, 2014, (12 pages).
Non-Final Office Action dated Nov. 30, 2016 for U.S. Appl. No. 14/543,787.
Final Office Action dated Jun. 12, 2017 for U.S. Appl. No. 14/543,787.
International Search Report and Written Opinion dated Nov. 19, 2015, International Patent Application No. PCT/US15/027670 with International Filing Date of Apr. 24, 2014, (18 pages).
Non-Final Office Action dated Apr. 14, 2017 for U.S. Appl. No. 14/696,342.
Amendment Response to Non-Final Office Action for U.S. Appl. No. 14/696,342, dated Jul. 14, 2017.
Amendment Response to Non-Final Office Action for U.S. Appl. No. 14/543,787, dated Feb. 28, 2017.
U.S.; Amendment Response to Non-Final Office Action dated Aug. 2, 2017 for U.S. Appl. No. 14/321,735.
U.S.; Final Office Action dated Aug. 4, 2017 for U.S. Appl. No. 14/696,342.
U.S.; Amendment Response to Non-Final Office Action dated Aug. 25, 2017 for U.S. Appl. No. 14/321,721.
U.S.; Amendment Response to Non-Final Office Action dated Aug. 25, 2017 for U.S. Appl. No. 14/321,729.
Notice of Allowance dated Aug. 31, 2017 for U.S. Appl. No. 14/321,735.
U.S.; Amendment Response to Final Office Action dated Sep. 11, 2017 for U.S. Appl. No. 14/543,787.
U.S.; Notice of Allowance dated Sep. 22, 2017 for U.S. Appl. No. 14/321,721.
U.S.; Notice of Allowance dated Sep. 22, 2017 for U.S. Appl. No. 14/321,729.

* cited by examiner

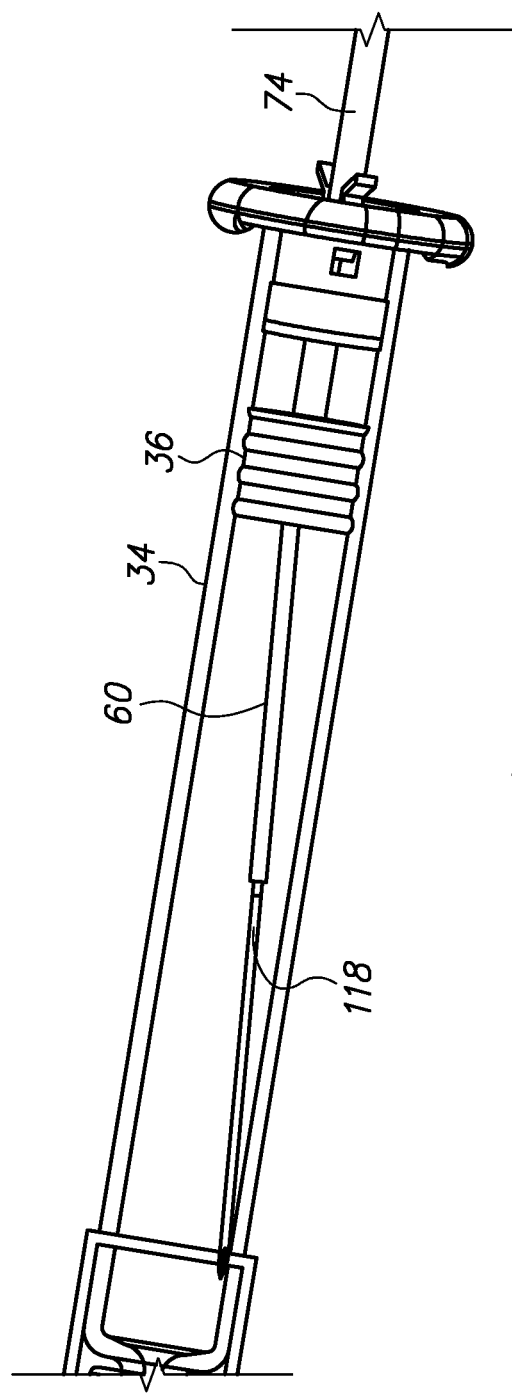

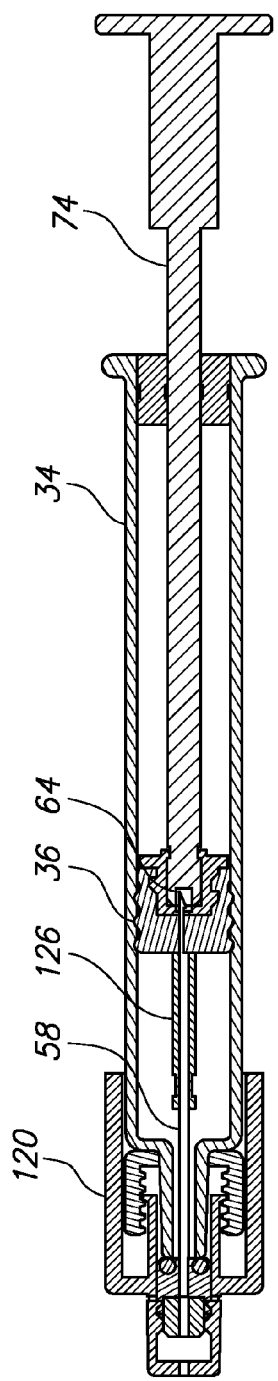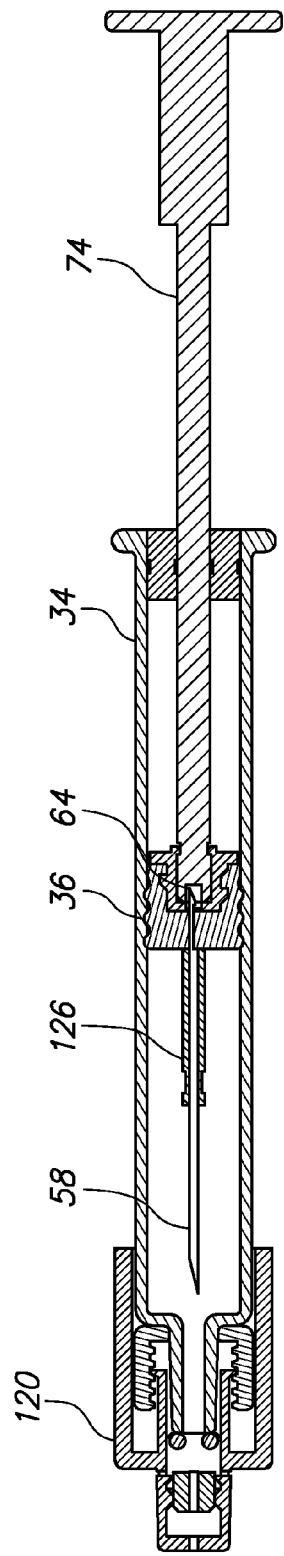
FIG. 12F
FIG. 12G

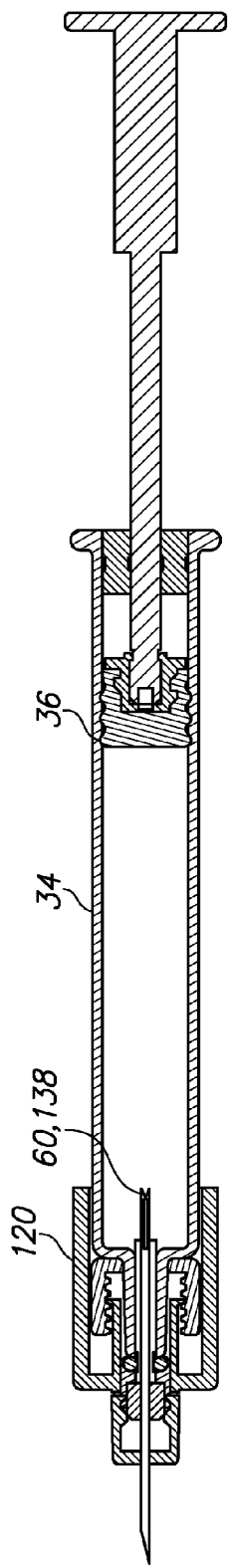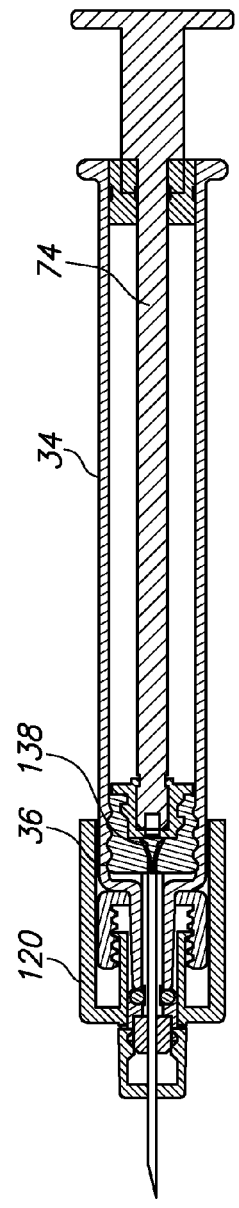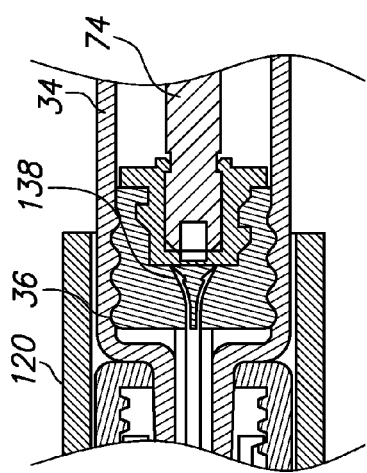
FIG. 16D
FIG. 16E
FIG. 16F

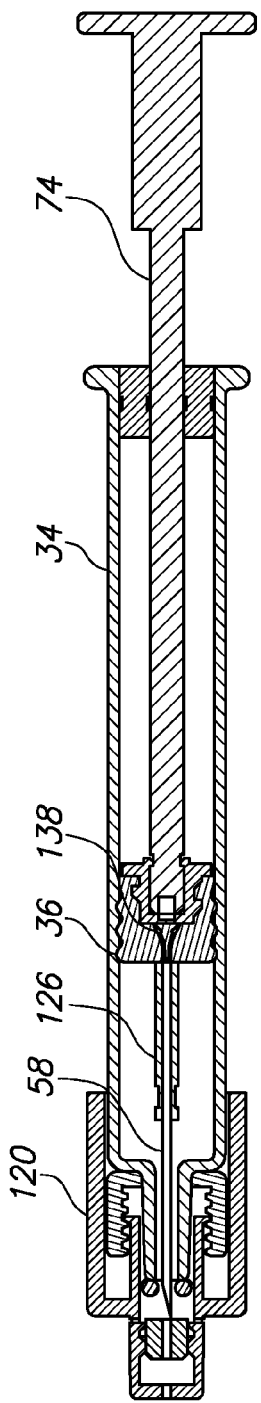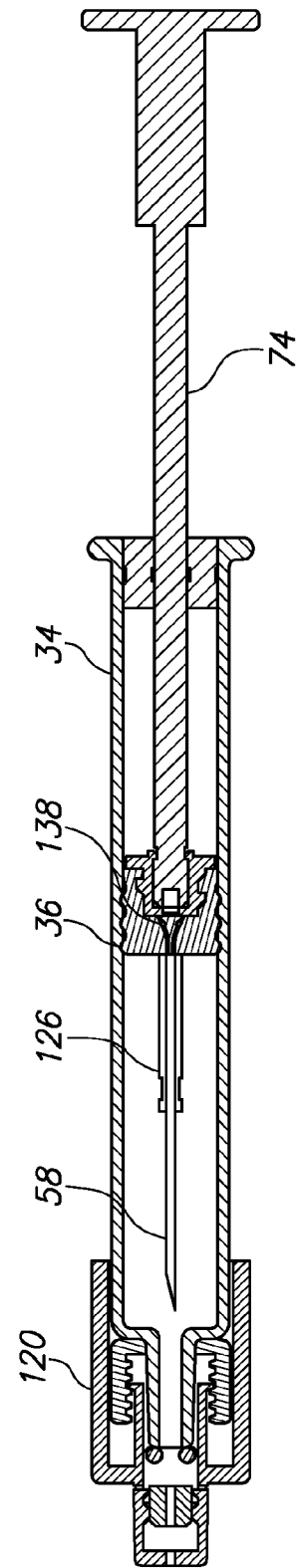

SAFETY SYRINGE

RELATED APPLICATION DATA

The present application claims the benefit under 35 U.S.C. §119 to U.S. provisional patent application Ser. No. 61/841,702 filed Jul. 1, 2013. The foregoing application is hereby incorporated by reference into the present application in its entirety.

FIELD OF THE INVENTION

The present invention relates generally to injection systems, devices, and processes for facilitating various levels of control over fluid infusion, and more particularly to systems and methods related to safety syringes in healthcare environments.

BACKGROUND

Millions of syringes, such as that depicted in FIG. 1A (2), are consumed in healthcare environments every day. A typical syringe (2) comprises a tubular body (4), a plunger (6), and an injection needle (8). As shown in FIG. 1B, such a syringe (2) may be utilized not only to inject fluid into a patient, but also to withdraw or expel fluid out of or into a container such as a medicine bottle, vial, bag, or other drug containment system (10). Indeed, due to regulatory constraints in some countries such as the United States as well as sterility maintenance concerns, upon use of a medicine bottle (10) with a syringe (2) as shown in a particular patient's environment, such medicine bottle may only be utilized with a single patient and then must be disposed of—causing significant medical waste from bottle and remaining medicine disposal, and even contributing to periodic shortages of certain critical drugs. Referring to FIG. 2A, three Luer-type syringes (12) are depicted, each having a Luer fitting geometry (14) disposed distally, so that they may be coupled with other devices having similar mating geometry, such as the Luer manifold assembly (16) depicted in FIG. 2B. The Luer fittings (14) of the syringes of FIG. 2A may be termed the "male" Luer fittings, while those of FIG. 2B (18) may be termed the "female" Luer fittings; one of the Luer interfaces may be threaded (in which case the configuration may be referred to as a "Luer lock" configuration) so that the two sides may be coupled by relative rotation, which may be combined with compressive loading. In other words, in one Luer lock embodiment, rotation, possibly along with compression, may be utilized to engage threads within the male fitting which are configured to engage a flange on the female fitting and bring the devices together into a fluid-sealed coupling. In another embodiment, tapered interfacing geometries may be utilized to provide for a Luer engagement using compression without threads or rotation (such a configuration may be referred to as a "slip-on" or "conical" Luer configuration). While such Luer couplings are perceived to be relatively safe for operators, there is risk of medicine spilling/leaking and parts breakage during the loading to provide a Luer coupling. The use of needle injection configurations, on the other hand, carries with it the risk of a sharp needle contacting or poking a person or structure that is not desired. For this reason, socalled "safety syringes" have been developed.

One embodiment of a safety syringe (20) is shown in FIG. 3, wherein a tubular shield member (22) is spring biased to cover the needle (8) when released from a locked position relative to the syringe body (4). Another embodiment of a safety syringe (24) is shown in FIGS. 4A-4B. With such a configuration, after full insertion of the plunger (6) relative to the syringe body (4), the retractable needle (26) is configured to retract (28) back to a safe position within the tubular body (4), as shown in FIG. 4B. Such a configuration which is configured to collapse upon itself may be associated with blood spatter/aerosolization problems, the safe storage of pre-loaded energy which may possible malfunction and activate before desirable, loss of accuracy in giving full-dose injections due to residual dead space within the spring compression volume, and/or loss of retraction velocity control which may be associated with pain and patient anxiety.

Further complicating the syringe marketplace is an increasing demand for pre-filled syringe assemblies such as that depicted in FIG. 5A, which generally comprise a syringe body, or "drug enclosure containment delivery system", (34), a plunger tip, plug, or stopper (36), and a distal seal or cap (35) which may be fitted over a Luer type interface. Liquid medicine may reside in the volume, or medicine reservoir, (40) between the distal seal and the distal end (37) of the plunger tip (36). Such assemblies are desirable because they may be standardized and produced with precision in volume by the few manufacturers in the world who can afford to meet all of the continually changing regulations of the world for filling, packaging, and medicine/drug interfacing materials selection and component use. Such simple configurations, however, generally will not meet the new world standards for single-use, safety, auto-disabling, and anti-needle-stick. Thus certain suppliers have moved to more "vertical" solutions, such as that (41) featured in FIG. 5B, which attempts to meet all of the standards, or at least a portion thereof, with one solution; as a result of trying to meet these standards for many different scenarios, such products may have significant limitations (including some of those described above in reference to FIGS. 3-4B) and relatively high inventory and utilization expenses.

There is a need for improved injection systems which address the shortcomings of currently-available configurations. In particular, there is a need for safety injection solutions which may utilize the existing and relatively well-controlled supply chain of conventionally delivered pre-filled syringe assemblies such as that described in reference to FIG. 5A.

SUMMARY OF THE INVENTION

One embodiment is directed to a safety syringe system, comprising: a syringe body forming a fluid reservoir and having proximal and distal ends; a plunger tip positioned within the fluid reservoir in a configuration such that medicinal fluid may be contained within the fluid reservoir; a needle assembly removably coupleable to the distal end of the syringe body such that the medicinal fluid may be transferred through a retractable needle coupled to a needle housing comprising the needle assembly upon insertion of the plunger tip relative to the syringe body; and a plunger control assembly coupled to the plunger tip and configured to facilitate manual insertion of the plunger tip relative to the syringe body; wherein upon insertion of the plunger tip to a final insertion state and release of an associated manual insertion load, a retraction load coupled between the syringe body and the plunger tip causes the plunger tip to be proximally withdrawn, pulling the retractable needle proximally relative to the needle housing to a retracted state wherein a distal tip of the needle becomes mechanically locked into an encapsulated configuration wherein it is no longer exposed for injection. The fluid reservoir may comprise a substantially cylindrical volume. The syringe body may comprise a glass material. The syringe body may comprise a polymeric material. The plunger tip may comprise an elastomeric material. The elastomeric material may comprise a butyl-based rubber. The needle may comprise a hypodermic needle. The hypodermic needle may comprise a standard size between about 20 gauge and about 34 gauge. The needle assembly may comprise a movable needle insertion-preventing member configured to prevent re-insertion of the needle relative to the syringe body after the needle has been placed in the retracted state. The insertion-preventing member may be configured to move along an axis that is substantially perpendicular to a longitudinal axis of the needle. The system further may comprise a releasing member operatively coupled to the insertion-preventing member and configured to remove a fixing constraint from the insertion-preventing member when the plunger tip reaches the final insertion state. The releasing member may comprise a push member configured to be compressively loaded when the plunger tip is urged into the final insertion state. The push member may be configured to release a mechanical latch configured to hold the needle fixed in place relative to the syringe body, thereby releasing the needle such that it may be proximally withdrawn into the retracted state. The mechanical latch may be configured to interface directly with the needle. The mechanical latch may be configured to interface with a needle interfacing member that is interfaced directly with the needle. The needle interfacing member may comprise a compliant O-ring. The plunger control assembly may comprise a plunger tip coupler member configured to be intercoupled with the plunger tip. The plunger tip coupler may comprise one or more helical threads configured to be inserted relative to the plunger tip to couple the plunger tip coupler to the plunger tip. The plunger tip coupler may be fixedly coupled to a plunger insertion member having a proximal end configured to be manually manipulated. The system further may comprise a plunger guiding flange through which the plunger insertion member is inserted, the plunger guiding flange being removably couplable to the proximal end of the syringe body. The retraction load may comprise a vacuum load. The retraction load may be developed by an integrated spring member. The retraction load may be developed manually. A brake assembly may be intercoupled between the plunger guiding flange and the plunger insertion member, the brake assembly being configured to prevent retraction of the plunger insertion member until after the first time it has been inserted to place the plunger tip in the final insertion state. The brake may be configured to reside in a braked state relative to the plunger guiding flange until the plunger insertion member is utilized to place the plunger tip in the final insertion state, after which the brake may be configured to mechanically transition to an unbraked state relative to the plunger guiding flange wherein it is configured to allow the plunger insertion member to be retracted away from the syringe body.

BRIEF DESCRIPTION OF THE DRAWINGS

FIGS. 12A-12G illustrate various aspects of a safety syringe configuration in accordance with the present invention.

FIGS. 16A-16H illustrate various aspects of a safety syringe configuration in accordance with the present invention.

DETAILED DESCRIPTION

Figure 6:
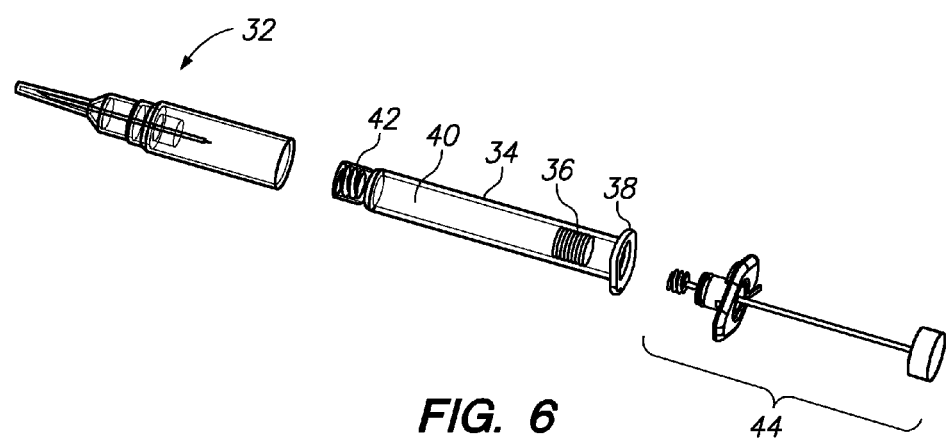
FIGS. 6-10K illustrate various aspects of a safety syringe configuration in accordance with the present invention.

Referring to FIG. 6, a disassembled view of a safety syringe assembly is illustrated, comprising a needle assembly (32) which may be removably coupled to an off-the-shelf syringe body (34) forming a reservoir (40) which may be at least partially pre-filled with a fluid such as a liquid medicine product. The distal end of the syringe body is configured to have a Luer type coupling interface (42), while the proximal end of the syringe body comprises a conventional syringe flange (38), such as that known as a "Gerresheimer" flange configuration. The syringe body (34) preferably comprises a translucent material such as a glass or polymer. To form a contained volume within the reservoir (40), and to assist with expulsion of the associated fluid through the needle, a plunger tip (36) may be positioned within the syringe body (34). The syringe body may define a substantially cylindrical shape (i.e., so that a plunger tip 36 having a circular cross sectional shape may establish a seal against the syringe body), or be configured to have other cross sectional shapes, such as an ellipse. A plunger control assembly (44) is configured to be coupled to the syringe body and to engage the plunger tip (36) to assist in expelling fluid from the syringe through the needle and in withdrawing the needle, as described below. As described above, the syringe body flange (38) may comprise a conventional flanged geometry which may be selected from the syringe body supplier; preferably the plunger control assembly (44) may be configured to be coupleable to many of the conventionally-available flange (38) geometries, such as various sizes of the flanges available from suppliers such as Gerresheimer, as noted above. The plunger tip (36) may comprise a standard butyl rubber material and may be coated, such as with a biocompatible lubricious coating, to facilitate preferred sealing and relative motion characteristics against the associated syringe body structure and material.

Figure 7A:
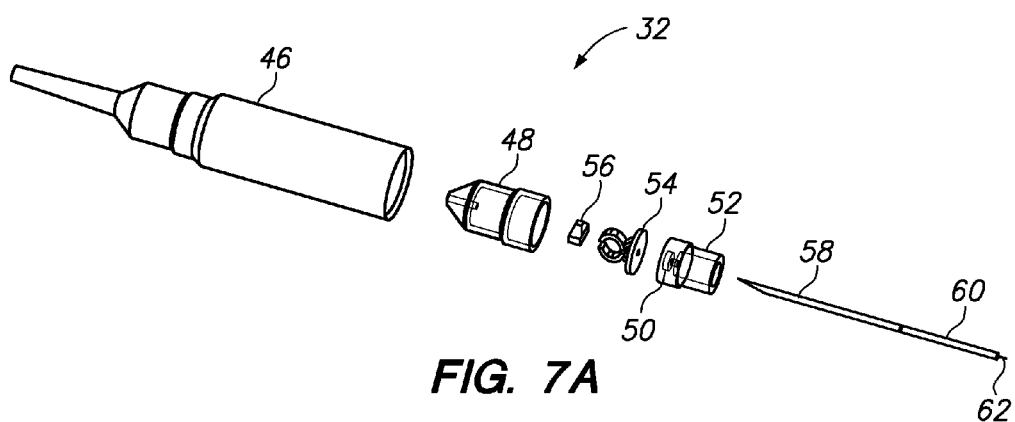

Referring to FIG. 7A, an exploded orthogonal view of an embodiment of a needle assembly (32) is illustrated showing a needle cover (46) configured to form a cover or shield over at least the distal end of the needle (58) when assembled. A distal needle housing member (48) and proximal needle housing member (50) assist in maintaining the position of the needle relative to the syringe body, and in controlling movement of a latch mechanism that comprises a two-fingered latch member (54) movably coupled to a movable needle insertion preventing member (56). The needle member has a sharpened distal end (58) configured to be inserted in a hypodermic fashion into a tissue structure of a patient; a proximal end (60) comprises a proximal tip interface (62) that may be configured to stab into and couple to a portion of an associated plunger tip, in a fashion that somewhat mimics the function of a harpoon instrument.

Figure 8:
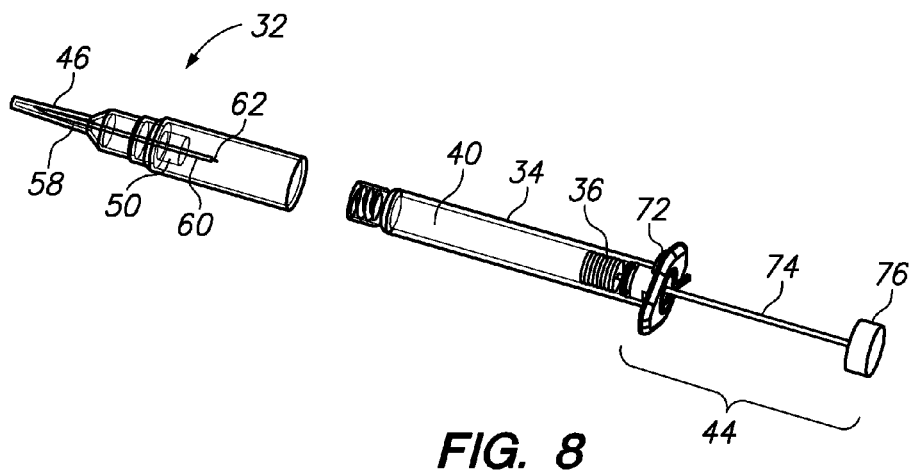

Referring to FIG. 7A, an exploded orthogonal view of an embodiment of a plunger control assembly (44) is illustrated showing a plunger insertion member (74) intercoupling a distally-disposed plunger tip coupler member (64), which may have outer helical threads configured to "screw into" and couple to the compliant material of an associated plunger tip as desired, a plunger insertion member proximal manipulation interface (76), a brake member (68), and a sealing flange assembly (66) comprising a flange member (72) configured to be removably coupled to the proximal flange fitting of a conventional syringe body (such as that shown in FIG. 6 as element 38) to hold into place a syringe body proximal plug member (88) with an additional sealing interface comprising an O-ring (70) to facilitate the buildup of a vacuum load when an associated plunger tip is inserted relative to the sealing flange assembly (88). The plunger insertion member proximal manipulation interface (76) preferably is shaped to allow for finger and/or thumb manipulation in a manner akin to that associated with operation of a conventional syringe (i.e., depression with a thumb or finger while one or more other fingers/digits are utilized to apply a counterload at the flange area). FIG. 8 illustrates a partially assembled configuration wherein a syringe body has been coupled to a plunger control assembly (44) with the plunger tip coupler member (64) helically advanced and coupled into the proximal aspect of the compliant plunger tip (36), and the flange member (72) coupled to the proximal flanged aspect of the syringe body (34). The needle cover (46) preferably is configured to shield/cover not only the distal aspect of the needle member (58), but also the proximal aspect (60, 62), in the depicted configuration, as shown, to enable an operator to manually grasp the needle assembly (32) as shown and couple it to the distal aspect of the syringe body (34) without placing the operator's fingers at risk for an accidental needle puncturing.

Figure 9A:
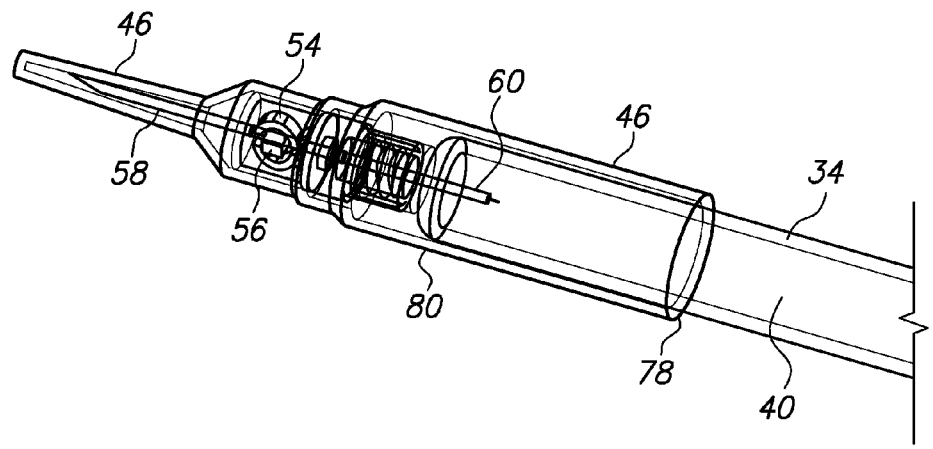

Referring to FIG. 9A, the fairly large overlap between the distal end (80) of the syringe body outer diameter and the interfacing end (78) of the needle cover provides a relatively large geometric guidance surface for aligning the needle proximal end (60) as it is guided through the needle assembly components during assembly/coupling with the syringe body (34) and guided into fluidic contact with the fluid reservoir of the syringe body (34).

Figure 7B:
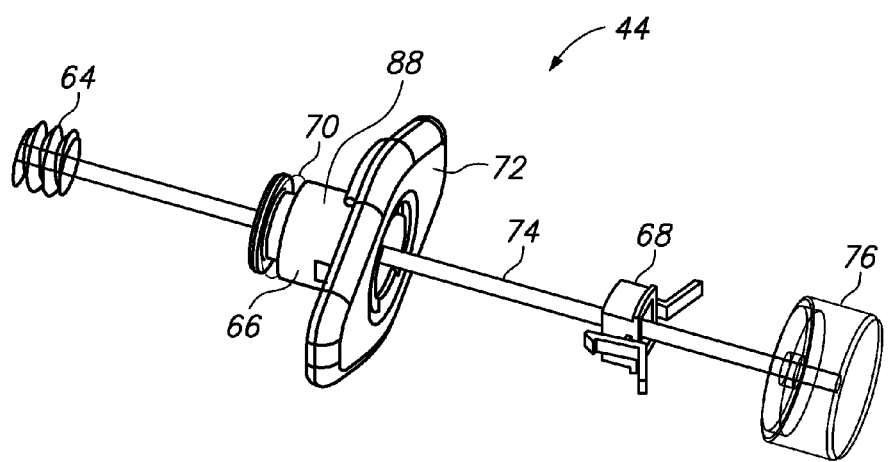
Figure 9B:
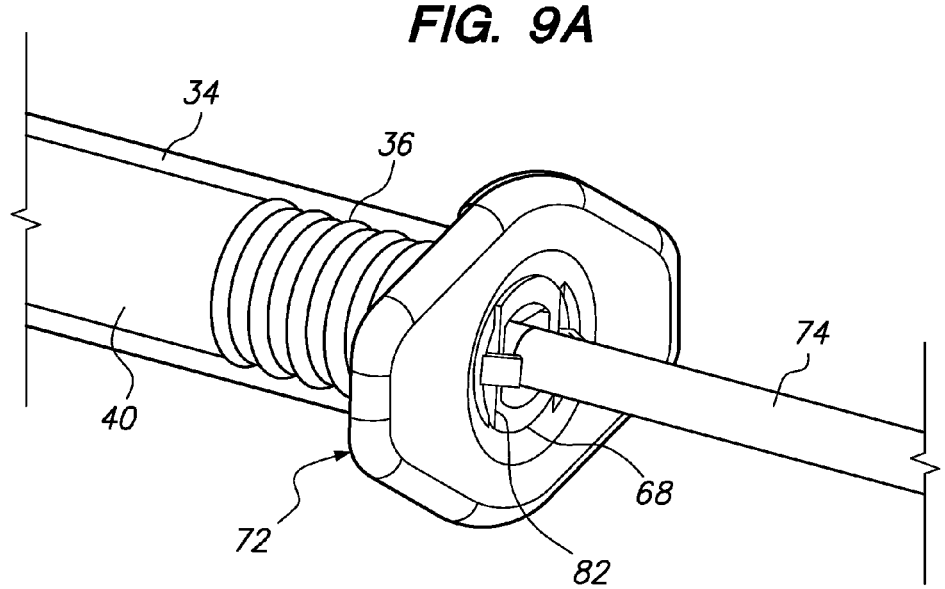
Figure 9C:
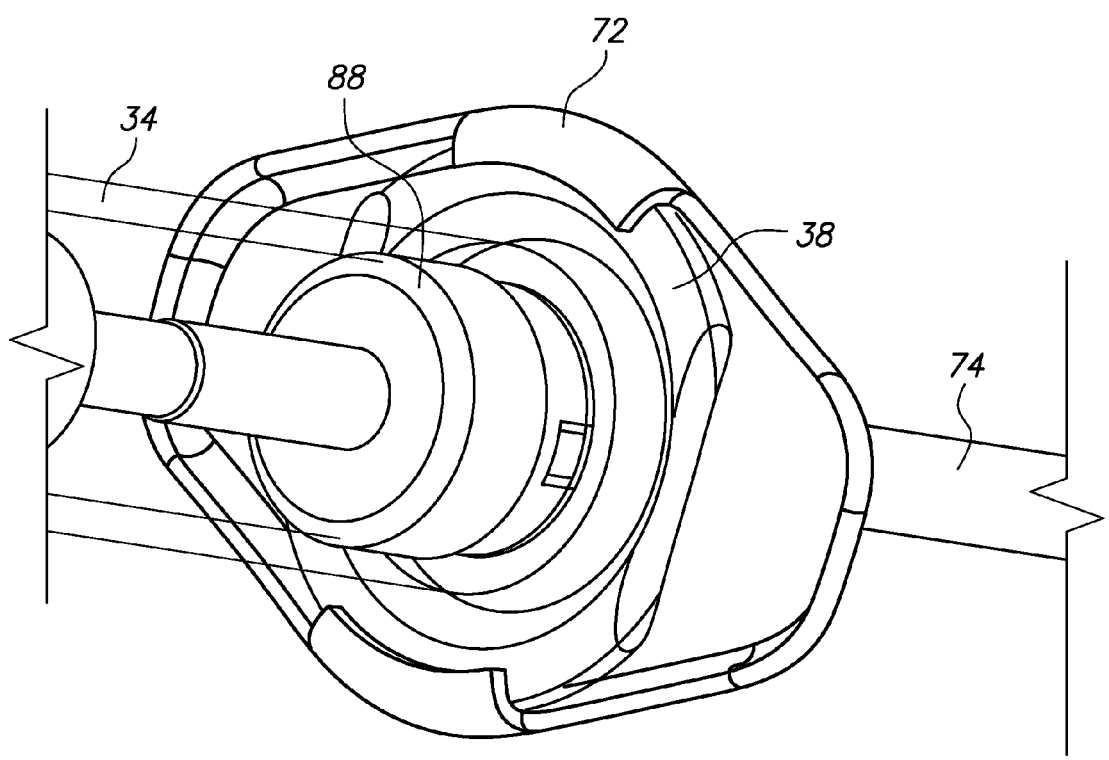
Figure 9D:
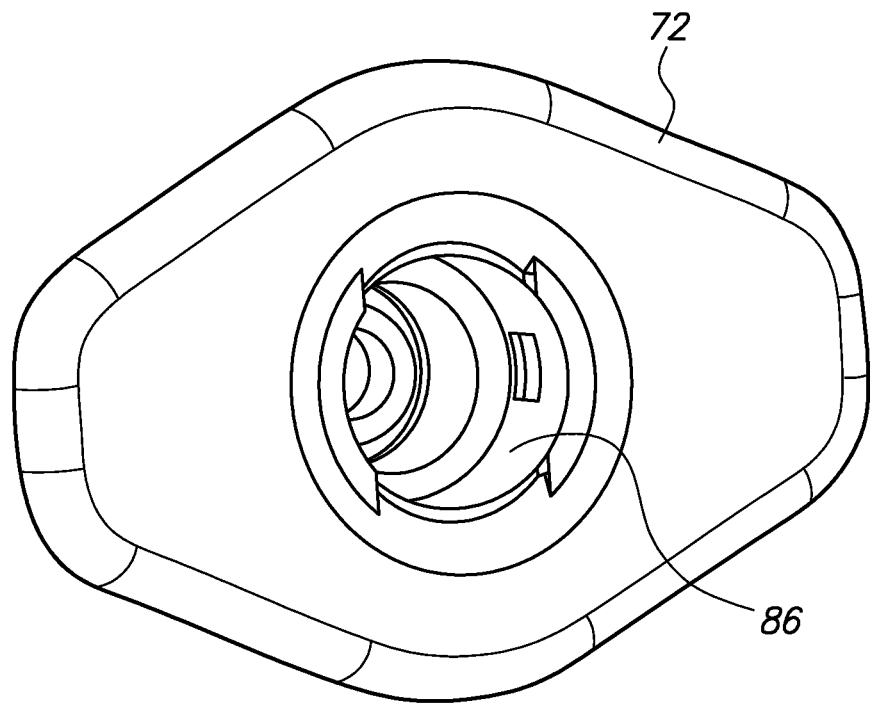
Figure 9E:
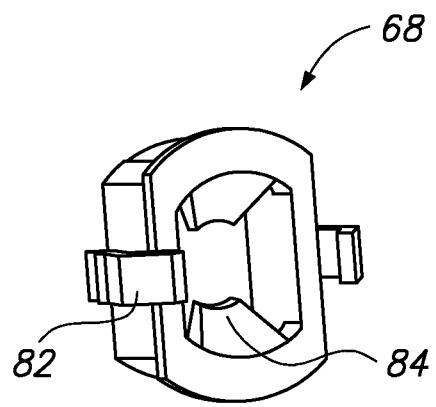

Referring to FIG. 9B, a flange member (72) is shown in relation to an intercoupled syringe body (34) and plunger insertion member (74). In the depicted embodiment, the mechanical interface between the plunger insertion member (74) and the flange member (72) is a brake member or brake assembly (68) which is configured to be snap-fitted into a recess formed into the flange member (72). FIG. 9C illustrates an opposing orthogonal view. FIG. 9D illustrates a flange member (72) without the brake member in place to show the recess surface (86) formed into the flange member (72). FIG. 9E shows a brake member (68) having two outer mounting release tabs (82) and two inner braking tabs (84). In this embodiment, the brake member (68) is configured to be snapped into the flange member recess (86) and held in place by geometric features coupled to the outer mounting release tabs (82). In such a position, the two inner braking tabs (84) are geometrically biased toward the distal end of the syringe body so that they will easily cantilever away from an inserted (i.e., inserted through the two inner braking tabs 84) plunger insertion member (element 74 in other drawings; not shown in FIGS. 9D and 9E) during such insertion with relatively low friction—but also resist retraction of the same plunger insertion member with relatively high loads until released from the coupling to the flange member (72). Such a release may be accomplished by depressing the two outer mounting release tabs (82)—and, indeed, these tabs (82) are configured to be automatically depressed for such a release upon full insertion of the plunger insertion member to a final insertion state wherein the associated plunger tip is interfaced against the end of the syringe and wherein the plunger insertion member proximal interface (element 76 in FIG. 7B, for example) is interfaced against the outer mounting release tabs (82) such that they are released, and the braking member (68) is allowed to travel along with the plunger insertion member, as shown in FIG. 10I, without further resisting retraction of the associated plunger insertion member.

Figure 10A:
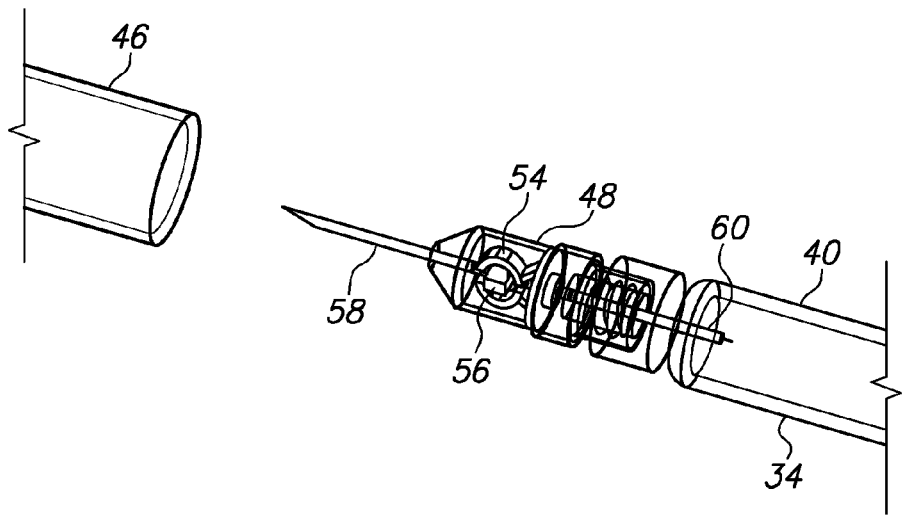
Figure 10B:
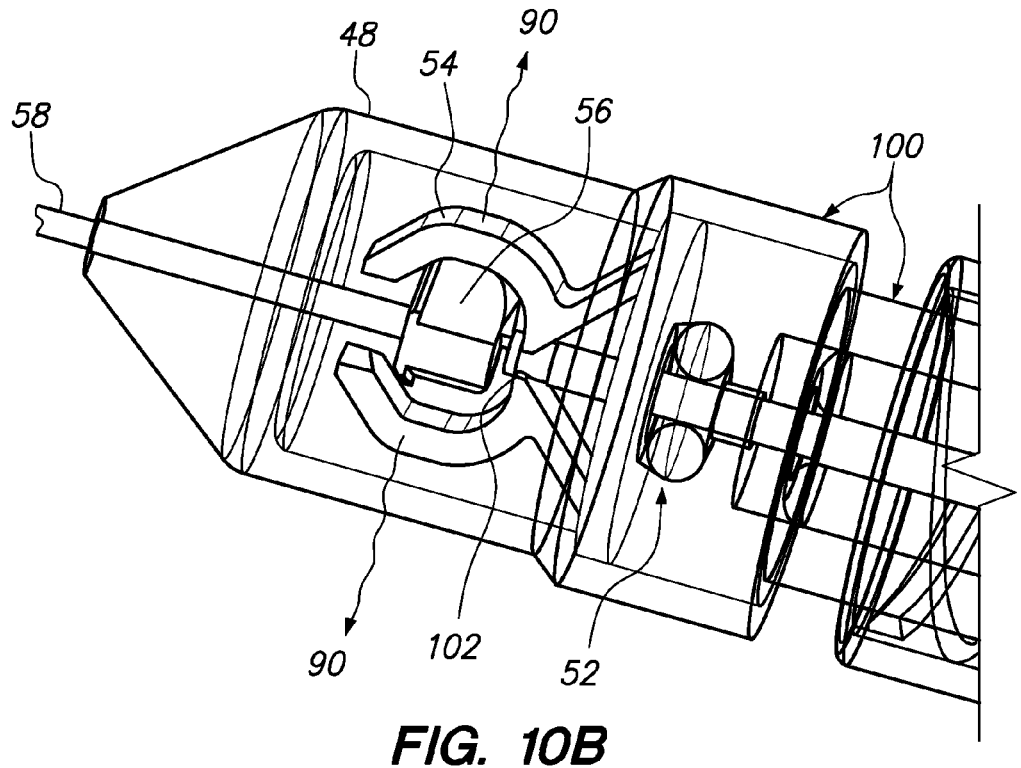
Figure 10C:
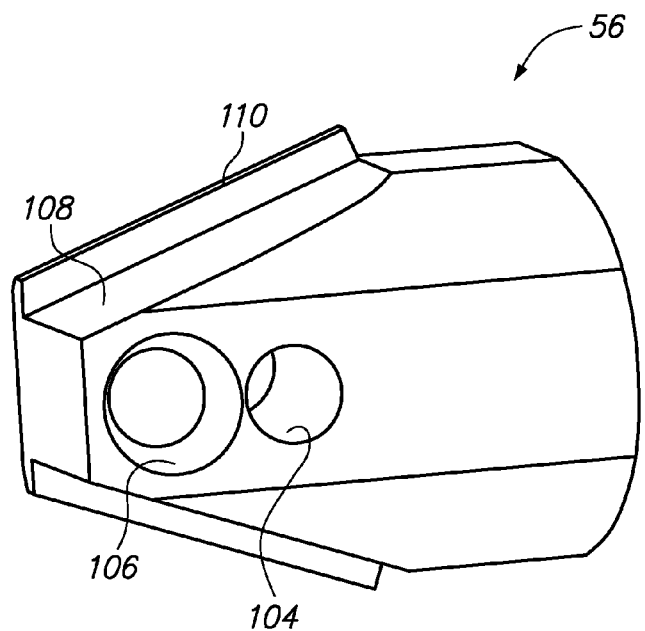
Figure 10D:
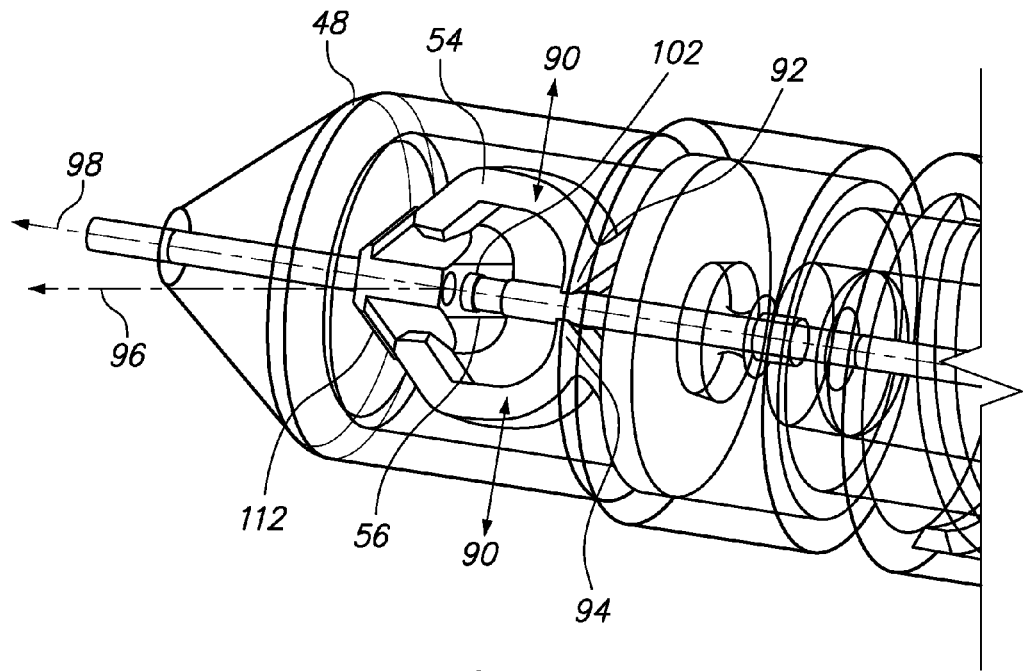
Figure 10E:
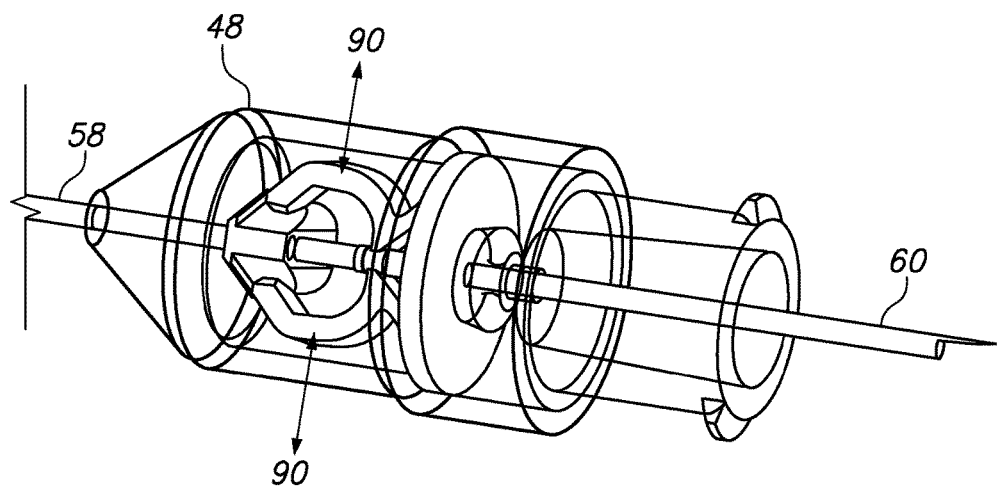
Figure 10F:
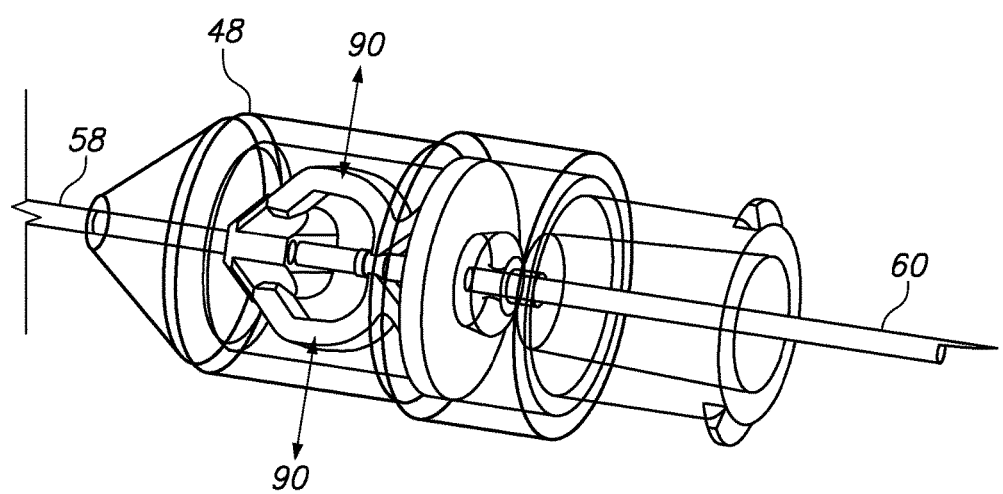
Figure 10G:
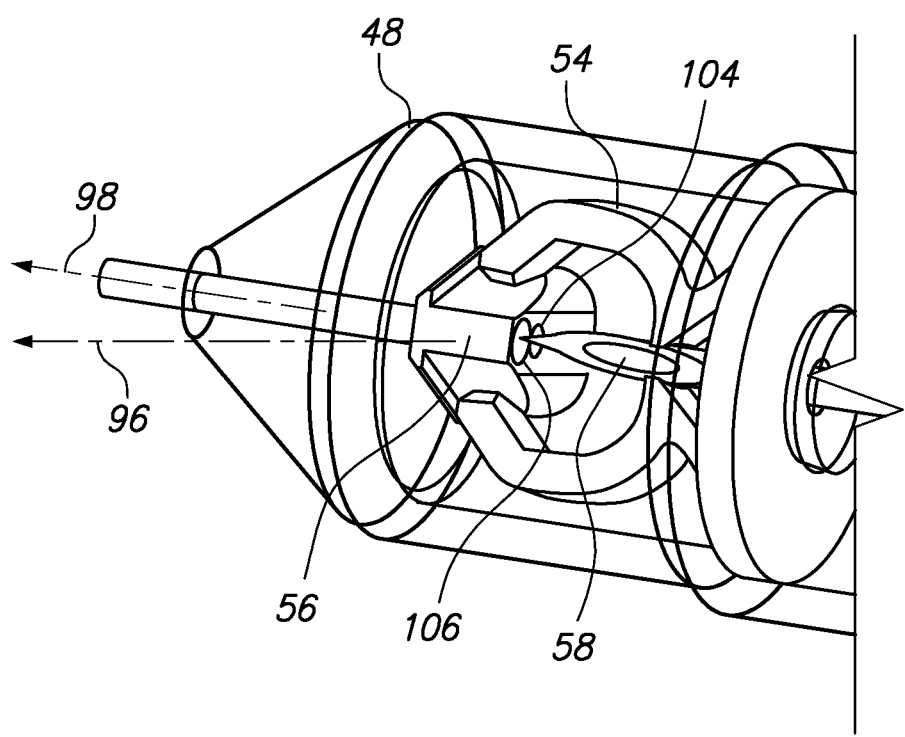
Figure 10H:
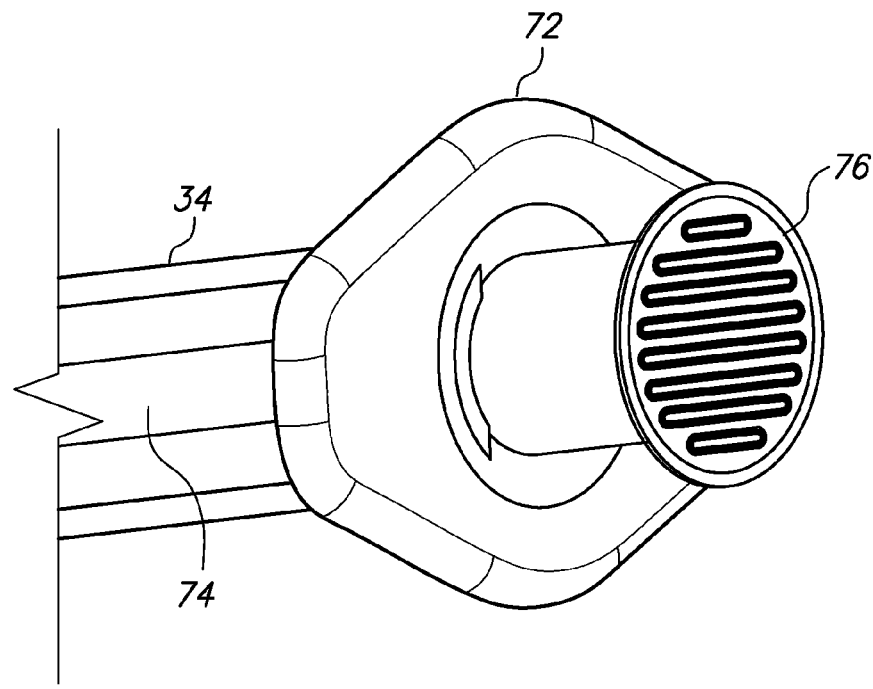
Figure 10I:
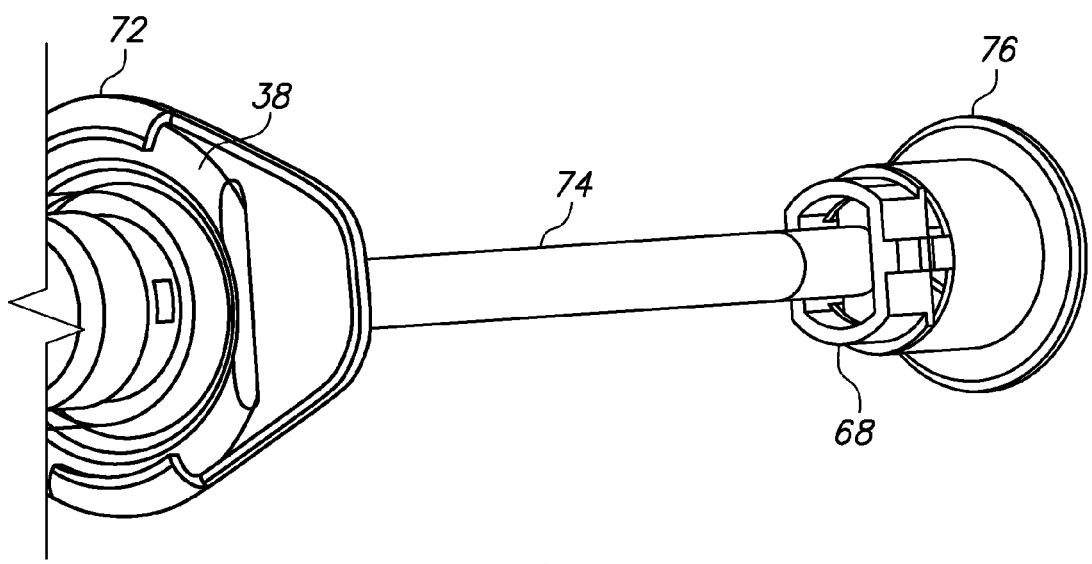

Referring to FIG. 10A-10K, various operational aspects of one embodiment of a safety syringe configuration in accordance with the present invention are illustrated. Referring to FIG. 10A, with a needle assembly coupled to a syringe body (34), the protective needle cover (46) may be removed as shown to expose the distal portion of the needle (58) for injection into a tissue structure of a patient. The internal support mechanisms of the needle assembly may be configured to support an injection load of about 5 pounds without yielding or slipping—to meet a standard such as those promulgated by organizations such as ISO. In the depicted embodiment, the proximal end (60) of the needle is configured to extend into the fluid reservoir (40) of the syringe body to become a fluid conduit for injection into a tissue structure that may be temporarily interfaced with a distal portion (58) of the needle. The needle is threaded through a movable needle insertion preventing member (56) which imparts only very minimal frictional loads to the needle in the depicted configuration wherein the needle is threaded directly through the needle insertion preventing member (56). Referring to the close-up view of FIG. 10B, with full insertion of the plunger tip to a final insertion state, the plunger is configured to impart a compressive load upon the needle and/or a sleeve coupled thereto, to urge the movable needle insertion preventing member (56) against the two fingers of the clip or latch member (54), thereby urging them away from each other (90). The geometry and structural moduli of these structures may be configured such that upon full insertion of the plunger tip to a final insertion state, a geometric step (element 110 as illustrated in FIG.

Figure 1A:
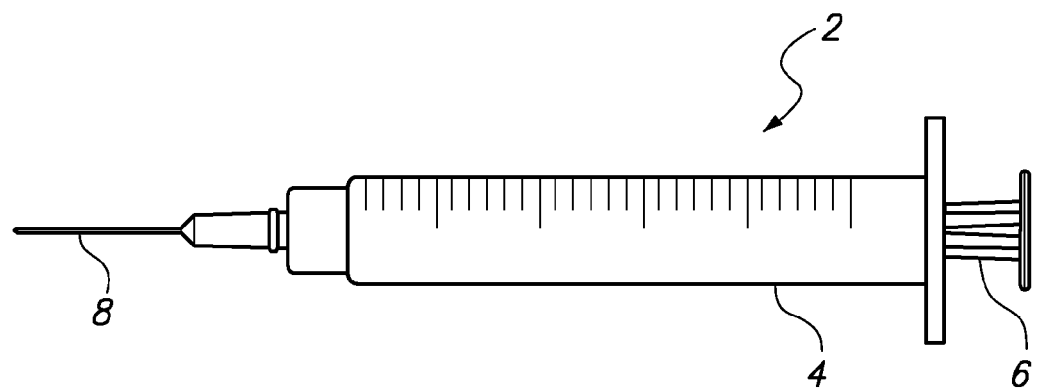
FIGS. 1-5B illustrate various aspects of conventional injection syringe configurations.
Figure 1B:
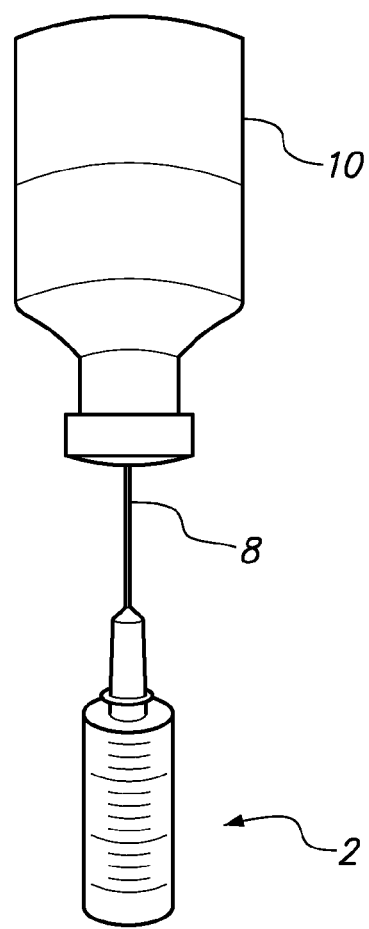
Figure 2A:
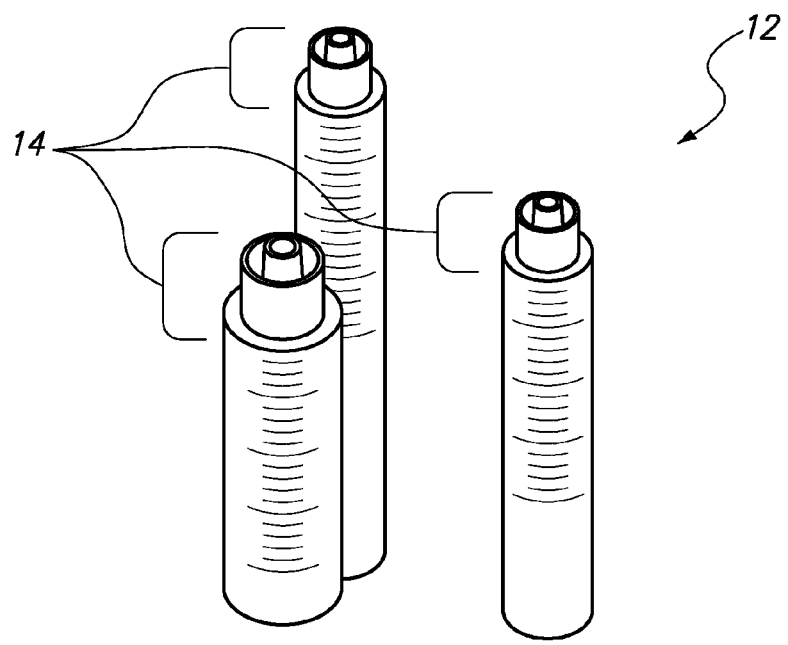
Figure 2B:
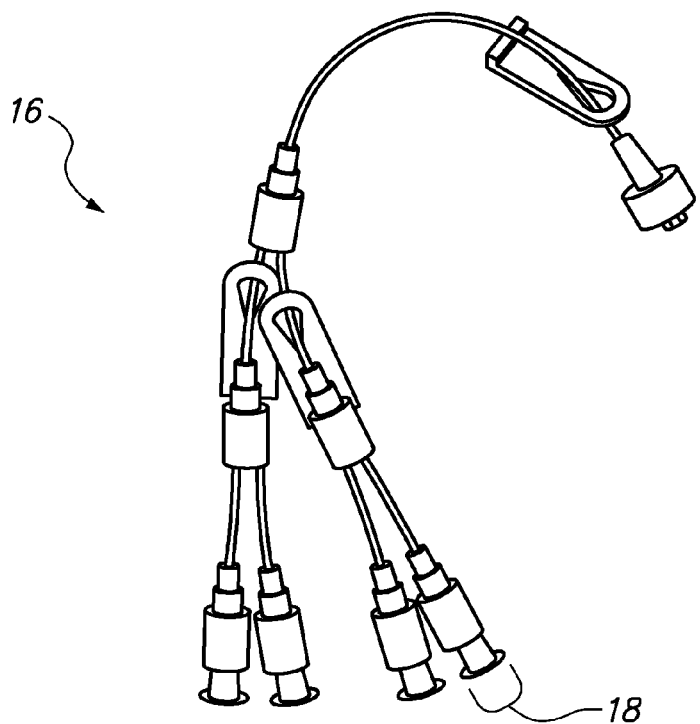
Figure 3:
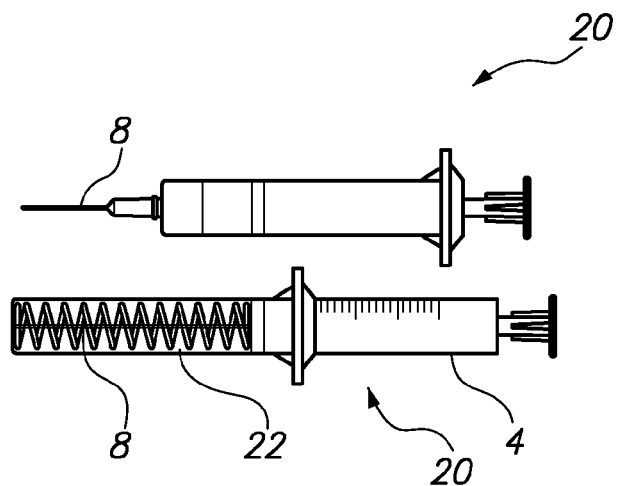
Figure 4A:
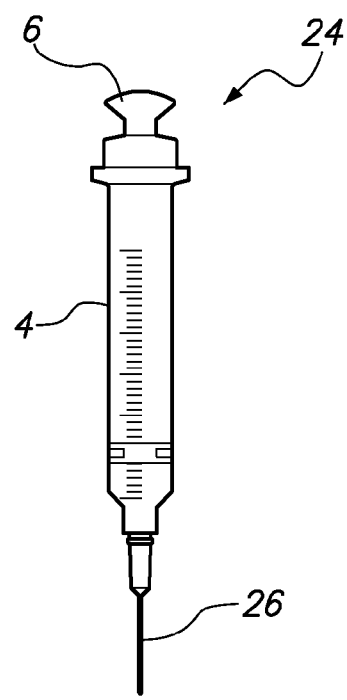
Figure 4B:
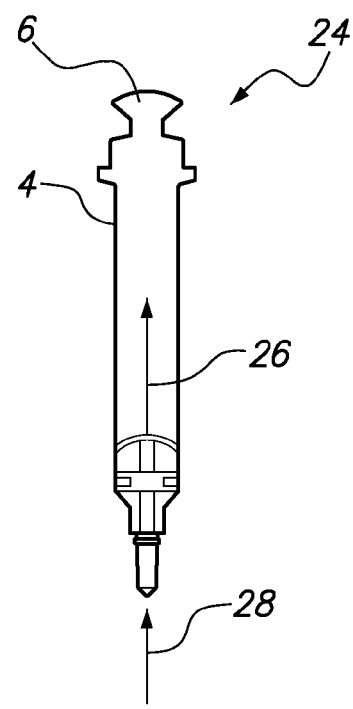
Figure 5A:
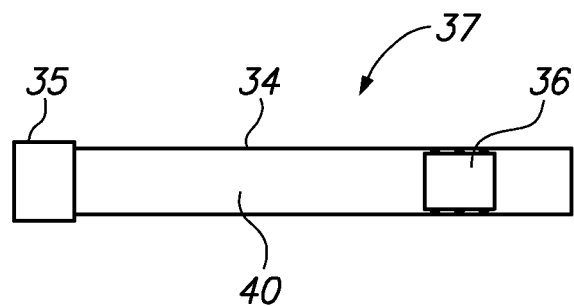
Figure 5B:
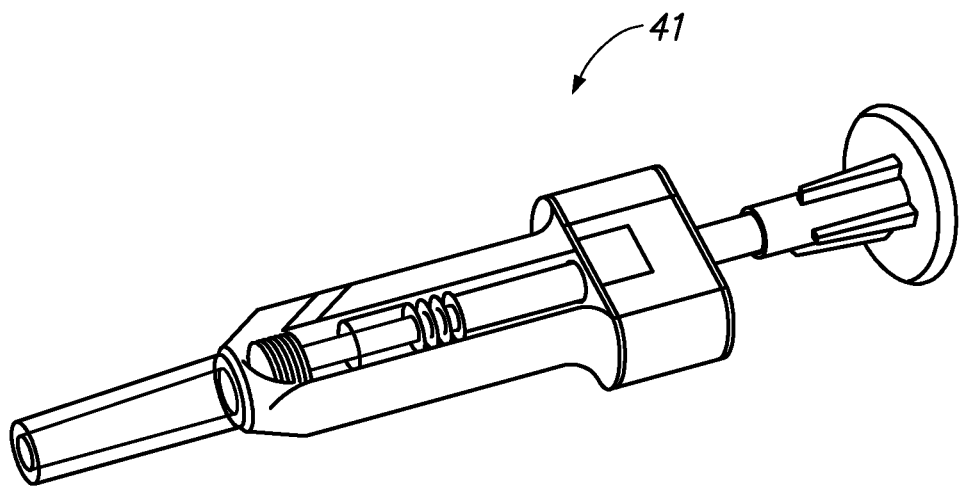
Figure 10J:
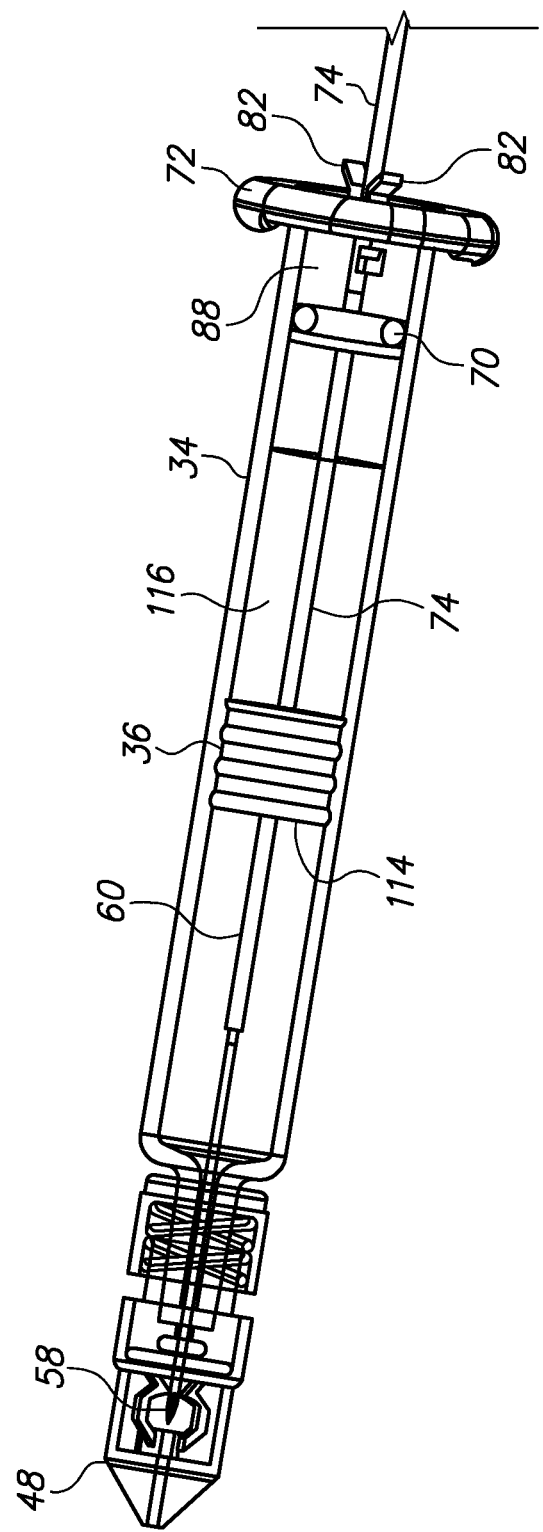

10C) of the movable needle insertion preventing member (56) is pushed past the two fingers of the latch member (54) so that the movable needle insertion preventing member (56) is stuck in a position, by virtue of the ramp surfaces (element 108 as illustrated in FIG. 10C), wherein it will remain biased open—and also biased to move in a direction (parallel to the axis 96 illustrated in FIG. 10D) substantially perpendicular to the longitudinal axis of the needle (element 98 in FIG. 10D, for example) if freed from the constraint of the needle passing through it. The movable needle insertion preventing member (56) may be slidably interfaced against, and retained by in the axial direction parallel to the longitudinal axis of the needle (98), a wall (112) formed in the distal needle housing member (48), as shown in FIG. 10D. With the two fingers of the latch member (54) biased open, a needle axial position constraining step (102) formed in the needle and/or a sleeve coupled to the needle may be freed from the constraint of the latch member (54) and allowed to retract, as shown in FIG. 10D, wherein the two latch contact points (92, 94) have been pulled apart enough that the needle is being withdrawn, here by vacuum load built up within the proximal aspect of the syringe body during insertion of the plunger tip. FIGS. 10E and 10F illustrate sequential images wherein the movable needle insertion preventing member (56) has been pushed past the two latch member (54) fingers to leave them permanently relatively open to that the needle may be retracted. Referring to FIG. 10G, with sufficient retraction of the needle so that the needle tip (58) is no longer threaded through a first needle through-aperture (104) and constraining the motion of the movable needle insertion preventing member (56), the movable needle insertion preventing member (56) is urged by compressive loading of the latch member (54) fingers on the ramped geometry of the movable needle insertion preventing member (56) to move along the depicted axis (96) which is substantially perpendicular to the needle longitudinal axis (98), thereby placing the needle distal tip (58) in alignment with the partial-depth needle aperture (106), which is configured to specifically block and constrain the needle distal tip (58) as a successive attempt is made to try to insert the needle. FIGS. 10H-10J illustrate various aspects of the plunger control assembly in relation to the syringe body (34). Referring to FIG. 10k, upon full retraction of the needle into the body of the syringe (34), the needle may be allowed to rest, or be biased to rest, in a canted or intentionally misaligned position relative to the syringe body (34) to prevent re-insertion of the needle relative to the syringe body (34). In use, the embodiments featured in FIGS. 10A-10K may function as follows: an off-the-shelf pre-filled syringe body, such as that described in reference to FIG. 5A, may be coupled to a plunger control assembly and needle assembly near the intended use location; the protective needle cover may be removed, and the patient injected with the needle, followed by insertion of the plunger tip to expel the syringe fluid into the patient; as the plunger tip is seated into the distal end of the syringe body, several events are intended to occur: a) the proximal end of the needle is harpooned into the plunger tip to couple these two structures; b) a plunger retraction brake is released by interfacing of the plunger insertion member proximal interface and brake member outer tabs so that the plunger insertion member and intercoupled plunger tip and harpooned needle may be withdrawn relative to the syringe body; c) a vacuum load is maintained by a substantially sealed proximal volume between the flange assembly (66) and the plunger tip which is expanded as the plunger tip is inserted; d) a movable needle retraction-preventing member (56) urges open the fingers of the associated latch member (54) to allow the needle to become relatively unconstrained in terms of proximal retraction or withdrawal into/toward the syringe body—and upon enough retraction of the needle (i.e. via the vacuum load pulling the plunger tip, which is harpoon-coupled to the needle so that the needle is pulled along proximally into retraction), the movable needle retraction-preventing member (56) moves over to block further re-insertion of the needle tip. Thus a single-use safety syringe configuration is described wherein a single injecting insertion is made relatively simple, while various mechanisms interact to allow for a controlled retraction of the needle and prevention of re-insertion after retraction. During the injecting insertion, the braking member of the plunger control assembly allows an operator to remove his hands completely from the system while the brake retains the position of the plunger tip relative to the syringe body. The braking member also may be effective in retaining the geometric relationship between a plunger tip and an associated syringe body and captured pre-filled medicine volume during shipping and handling before utilization. For example, with conventional configurations, such as that shown in FIG. 5A, it is possible that changes in pressure, such as those created with air transport, may move the plunger tip relative to the syringe body—possibly past the acceptable sterile geometric boundaries/barriers. Such relative motion may be prevented with a locking/braking configuration as described herein.

Figure 11:
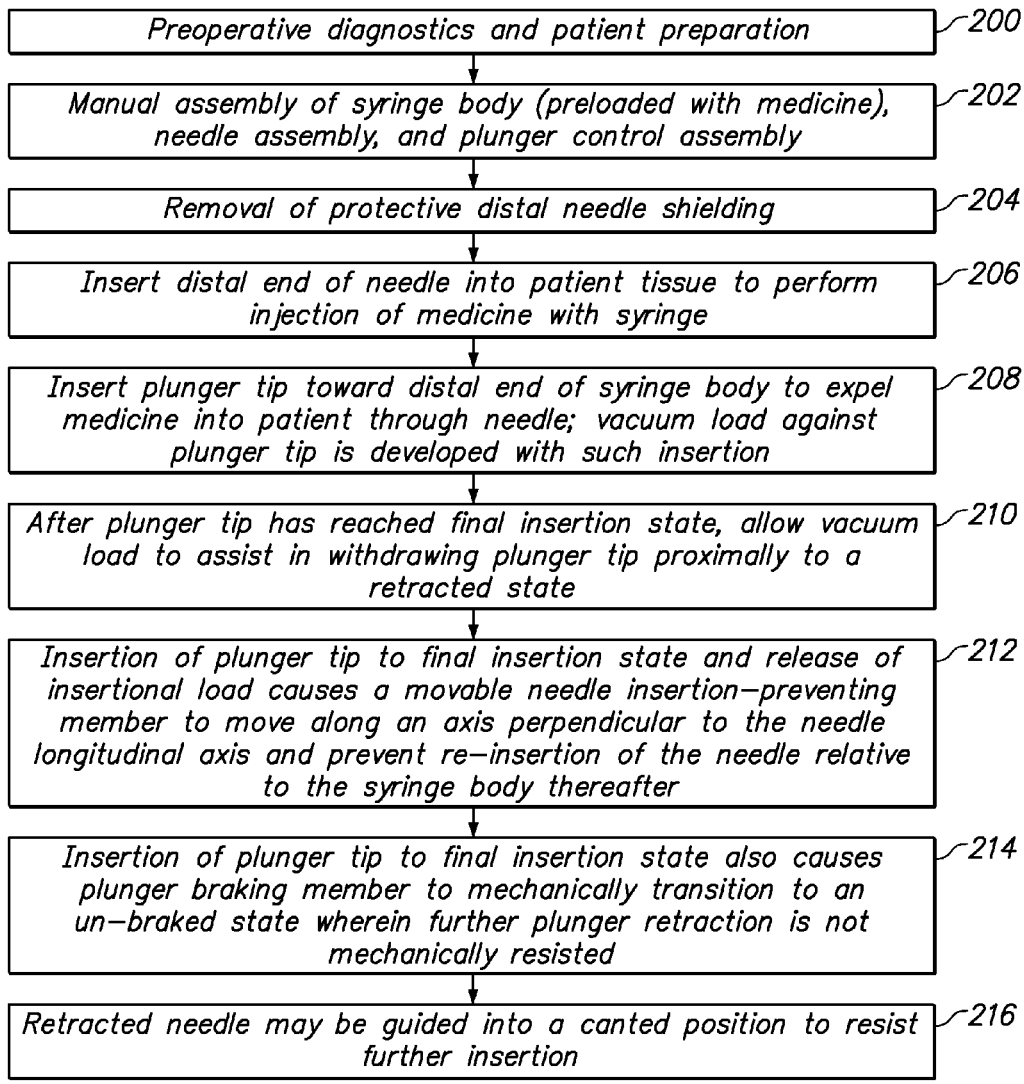
FIG. 11 illustrates a process for conducting an injection procedure utilizing a safety syringe configuration such as that described in reference to FIGS. 6-10K.

Referring to FIG. 11, a process is illustrated for using an embodiment such as that described in reference to FIGS. 10A-10K. After preoperative diagnostics and patient preparation (200), an safety syringe injection assembly may be assembled (202). When an injection is desired, the protective needle cover may be removed (204) and the injection performed upon a tissue structure of the patient (206, 208). After the plunger tip has reached a final insertion state, the built up vacuum load may be utilized to assist in withdrawing the plunger tip proximally to a retracted state (210); such insertion to the final insertion state and subsequent retraction of the needle may cause movement of the movable needle insertion-preventing member to move into a configuration wherein it will prevent re-insertion of the needle (212); insertion of the plunger tip to the final insertion state also causes the plunger braking member to mechanically transition to an un-braked state wherein plunger retraction is not mechanically resisted by the brake (214). The retracted needle may be fully retracted into the syringe body and positioned in a canted configuration to prevent further insertion (216).

Referring to FIGS. 12A-12G, another embodiment is depicted wherein a mechanism is configured to allow for a full injection insertion, after which the needle may be automatically withdrawn, and in certain embodiments, also prevented from re-insertion. For simplicity of illustration, braking features, such as those described in reference to FIGS. 9A-10K, are not shown in the embodiments of FIGS. 12A-12G, but they may be present in certain variations and configurations, and are described, for example, in the embodiment of FIG. 13.

Figure 12A:
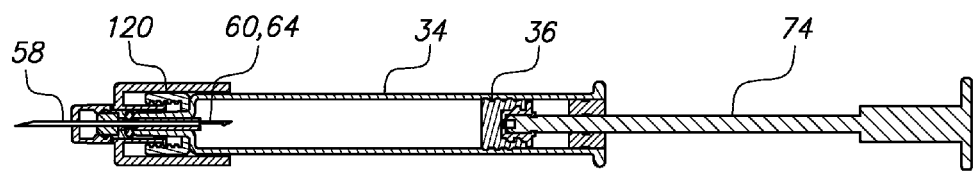
Figure 12B:
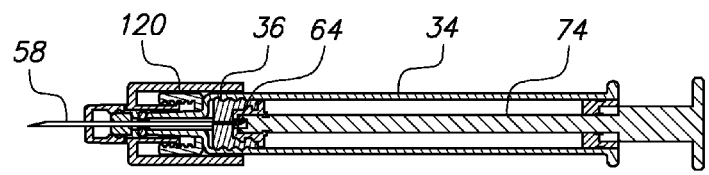
Figure 12C:
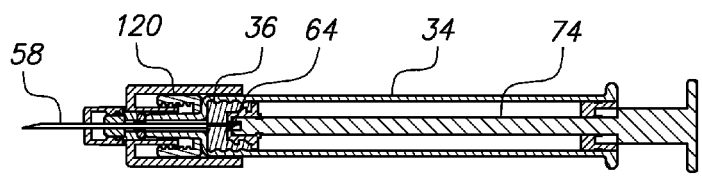
Figure 12D:
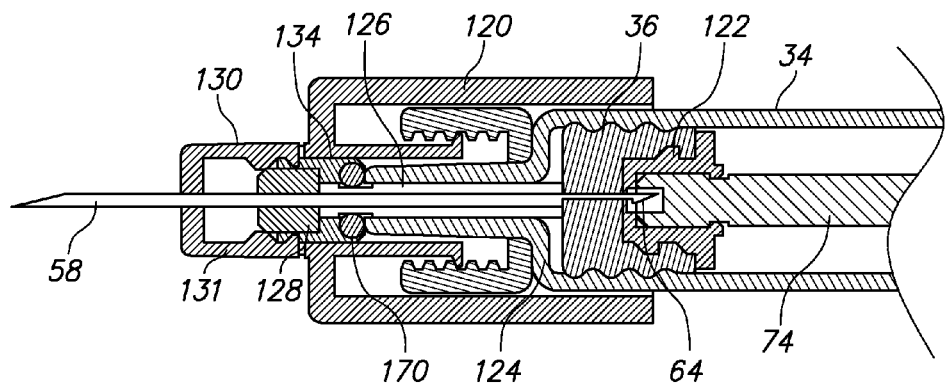
Figure 12E:
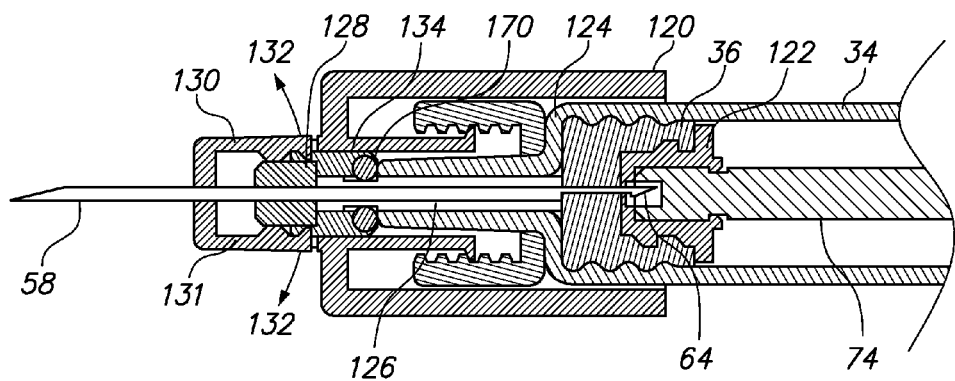

Referring to FIGS. 12A-12G, a safety syringe assembly is depicted wherein a needle housing (120) may be coupled to a conventional syringe body (34) and utilized to facilitate a single full insertion of the needle, after which needle withdrawal may be automatically facilitated by a combination of a withdrawal-prevention mechanism converting to a state wherein needle withdrawal is freely allowed, and a vacuum load developed in the captured volume proximal to the plunger tip in the syringe body being allowed to facilitate needle withdrawal, as described above. As shown in FIG. 12A, a plunger tip (36) is shown ready to inject the contents of the syringe body (34) into the needle, the distal portion (58) of which may be directly interfaced with a patient tissue structure. Referring to FIG. 12B, a close-up view of which is shown in FIG. 12D, with the plunger tip (36) almost fully inserted, the needle remains locked in place and prevented from withdrawal by a locking configuration comprising an O-ring forcibly urged against a needle sleeve (126) coupled to the needle. The proximal needle end (60) features a harpoon-like interface (64) configured to stab into the plunger tip (36) material and couple thereto. The depicted embodiment also features a polymeric backing (122) of the plunger tip (36) selected to create a more robust coupling of the needle and plunger tip. Referring to FIG. 12C, a close-up view of which is shown in FIG. 12E, with complete insertion of the plunger tip (36), the needle sleeve (126) urges a load-transferring member (128) at least partway through a plurality of latch members (130, 131), which rotate (132) as shown in FIG. 12E, to release an O-ring loading member (134) from its prior constraint up against the O-ring (170), allowing the O-ring to slightly relax and thereby free the needle of the previous axial withdrawal constraint, after which retraction of the plunger insertion member (74), such as by vacuum load or manually, will pull the needle into proximal withdrawal relative to the syringe body (34), as shown in FIGS. 12F and 12G.

Figure 13:
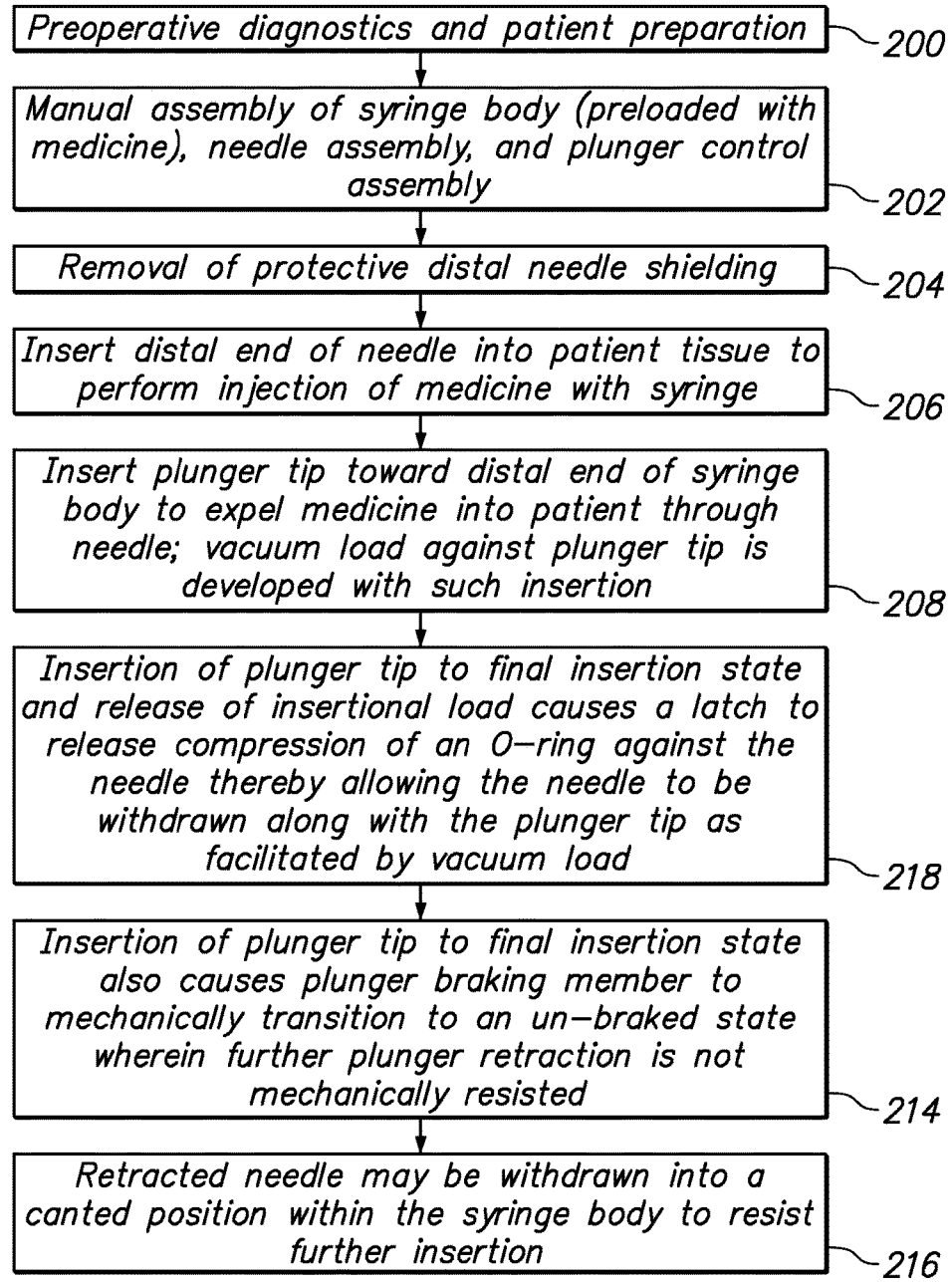
FIG. 13 illustrates a process for conducting an injection procedure utilizing a safety syringe configuration such as that described in reference to FIGS. 12A-12G.
Figure 14A:
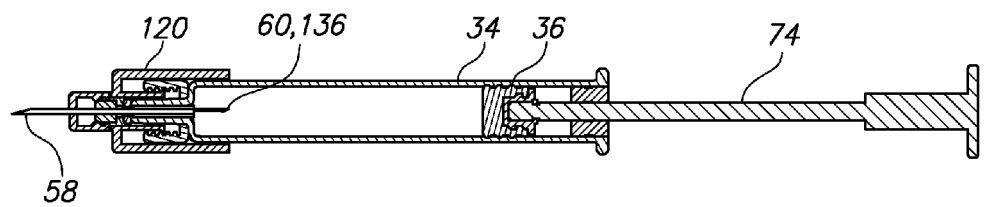
FIGS. 14A-14G illustrate various aspects of a safety syringe configuration in accordance with the present invention.
Figure 14B:
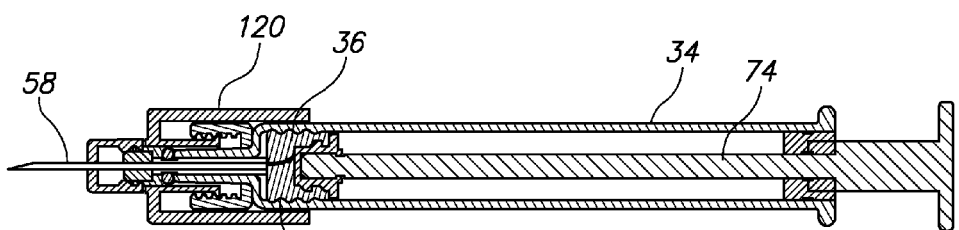
Figure 14C:
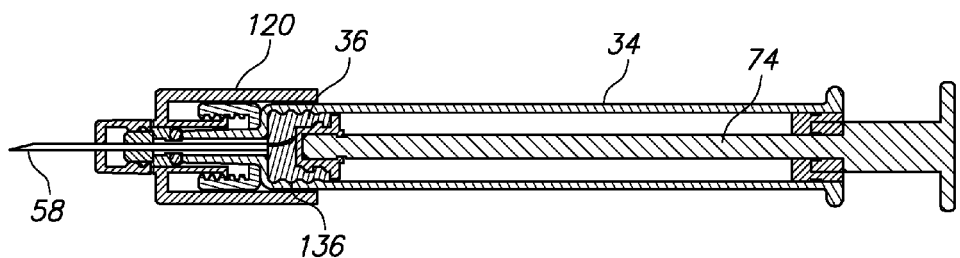
Figure 14D:
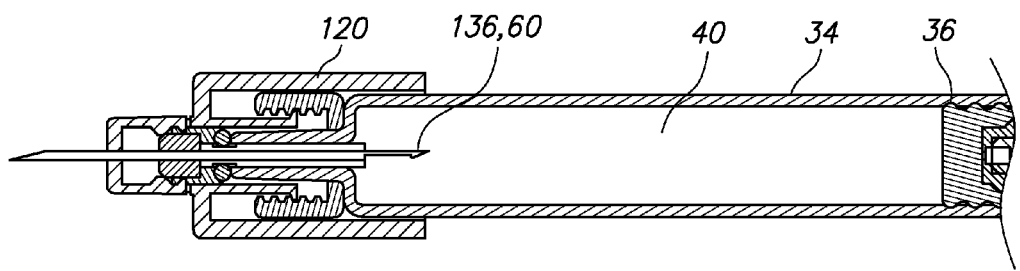
Figure 14E:
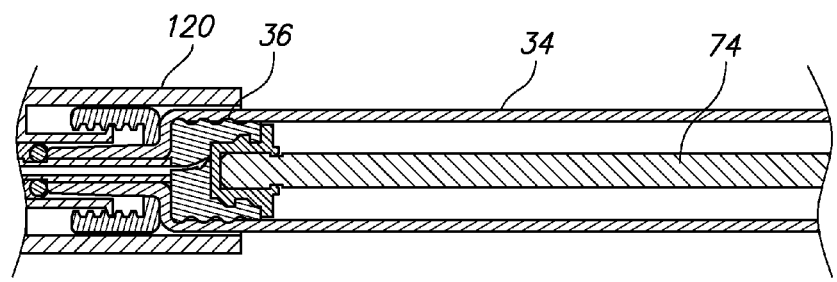
Figure 14F:
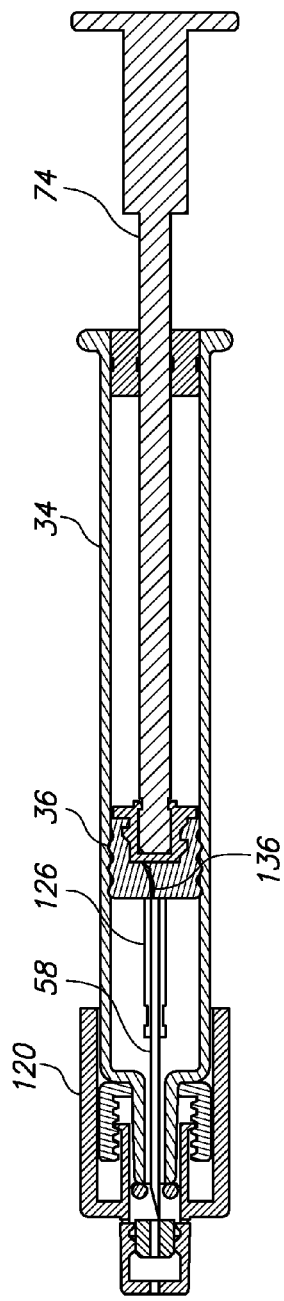
Figure 14G:
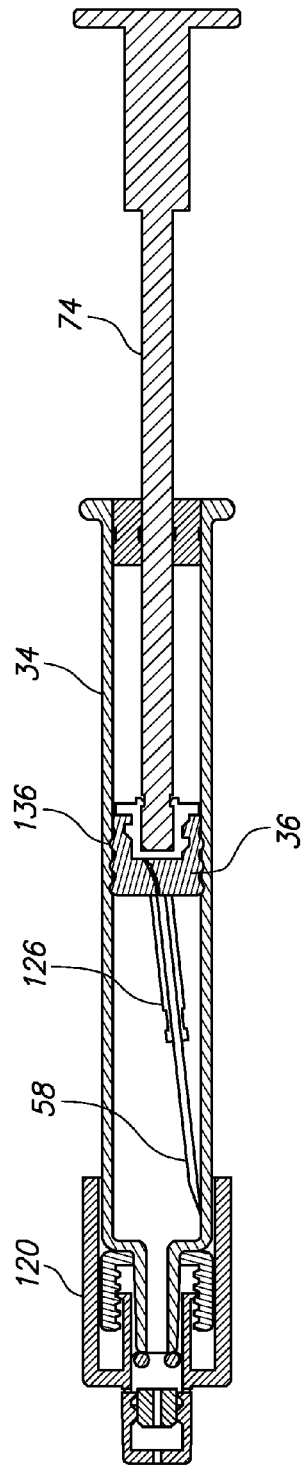

Referring to FIG. 13, an embodiment similar to that of FIG. 11 is illustrated, with the exception that in the embodiment of FIG. 13, after the injection insertion (208), insertion to a final insertion state releases compression of an O-ring from against the needle, thereby allowing the needle to be withdrawn (218), as described above in reference to FIGS. 12A-12G.

Figure 15:
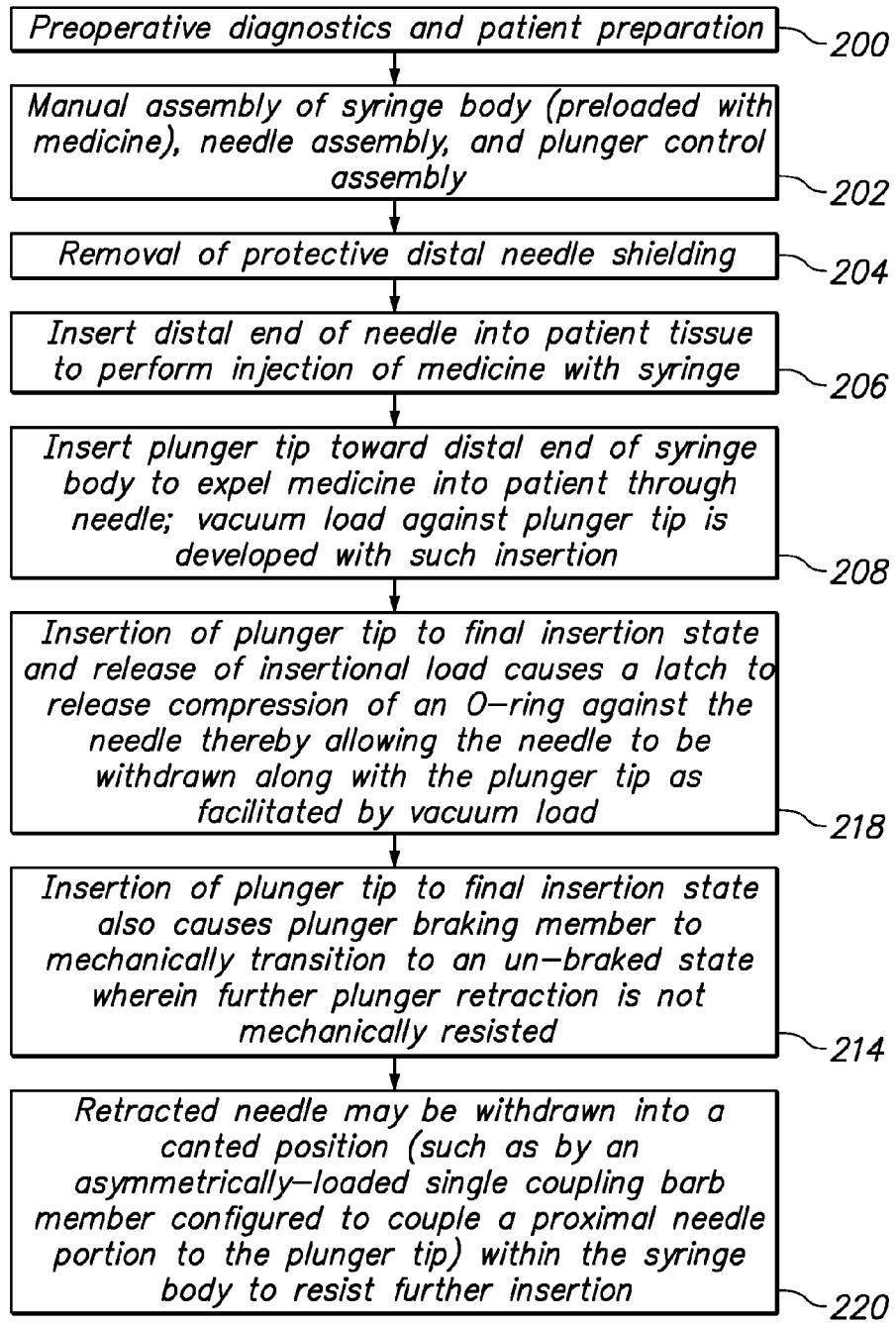
FIG. 15 illustrates a process for conducting an injection procedure utilizing a safety syringe configuration such as that described in reference to FIGS. 14A-14G.
Figure 16A:
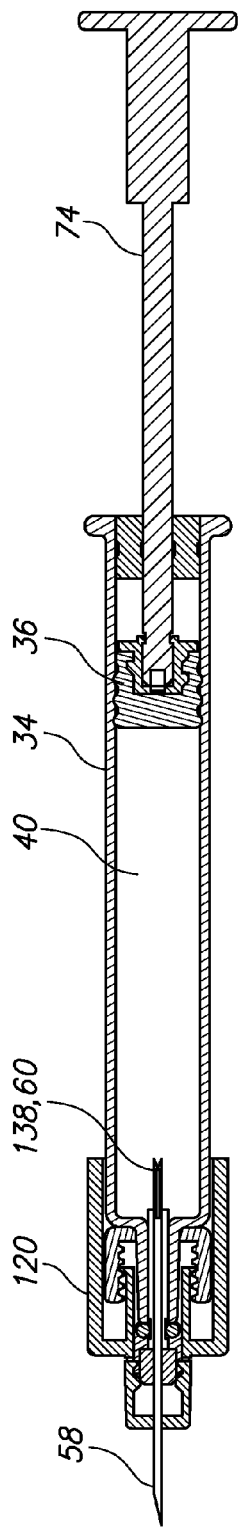
Figure 16B:
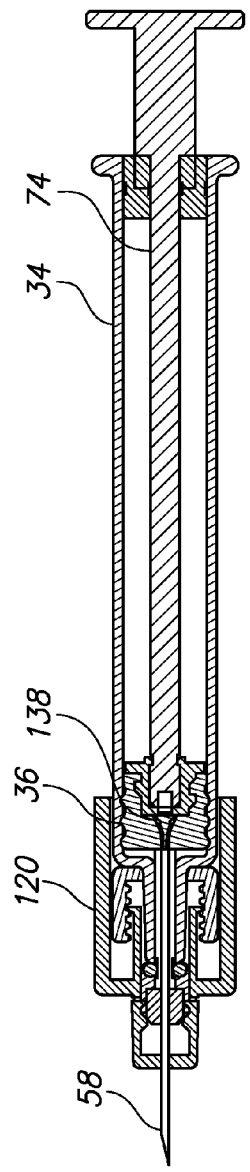
Figure 16C:
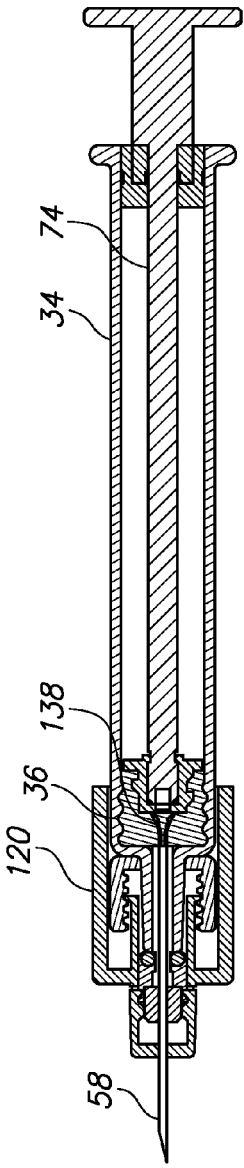

Referring to FIGS. 14A-14G, an embodiment similar to that of FIGS. 12A-12G is illustrated, with the exception that the embodiment of FIGS. 14A-14G features an off-axis or bent proximal harpooning or barb interface (136) that is configured to cause a fully-withdrawn needle to be canted to the side, or out of alignment relative to the syringe body (34), so that the needle cannot be re-inserted by another attempted insertion of the plunger tip. FIG. 15, which is similar to FIG. 13, features the addition of such misalignment of the needle member upon full withdrawal of the needle member into the syringe body (220) to prevent re-insertion of the needle member relative to the syringe body (i.e., to prevent re-use, or accidental/undesired contact of a needle tip with a person or object).

Figure 17:
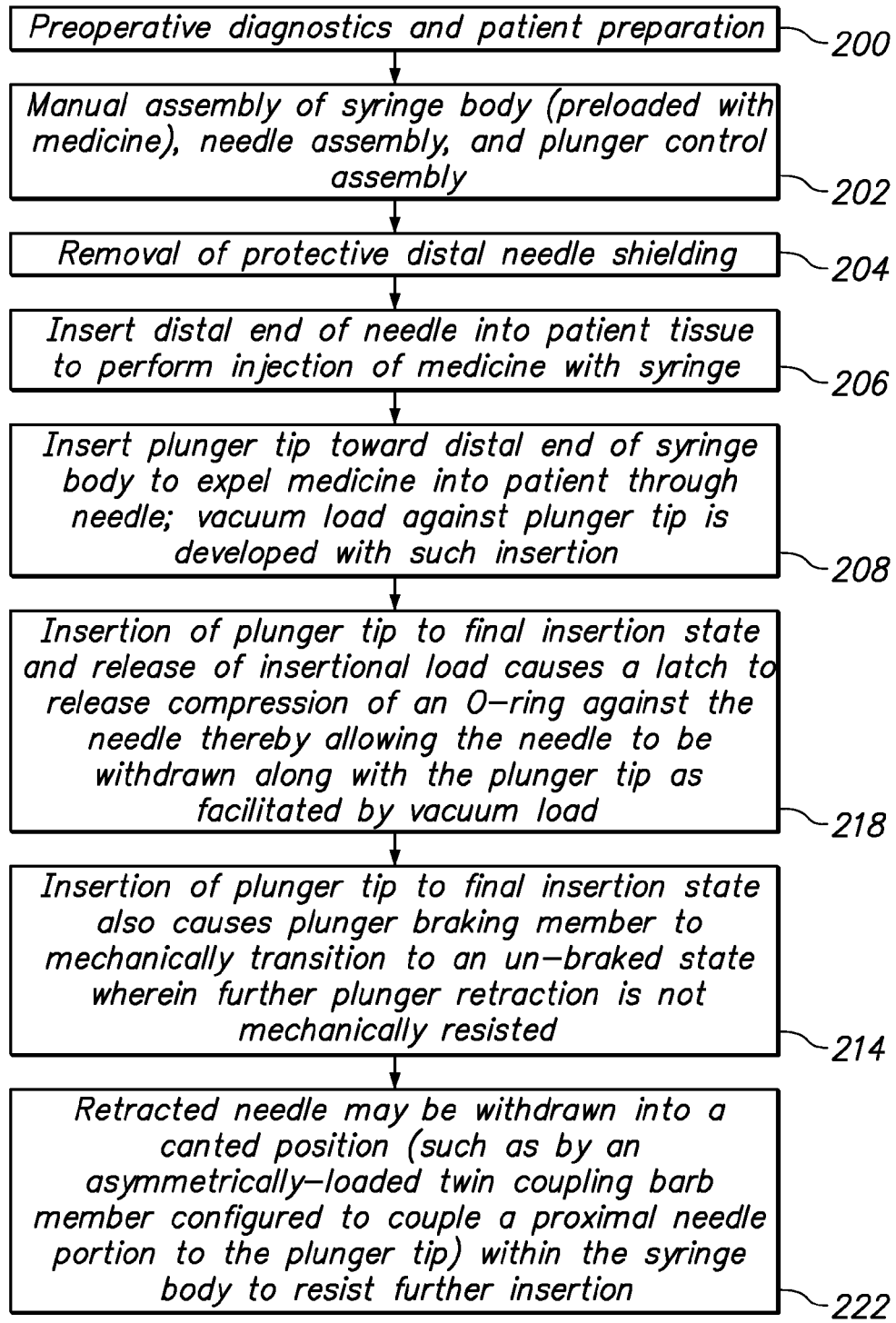
FIG. 17 illustrates a process for conducting an injection procedure utilizing a safety syringe configuration such as that described in reference to FIGS. 16A-16H.

Referring to FIGS. 16A-16H, an embodiment similar to that of FIGS. 12A-12G is illustrated, with the exception that the embodiment of FIGS. 16A-16H features double off-axis or bent proximal harpooning or barb interface (138) that is configured to cause a fully-withdrawn needle to be canted to the side, or out of alignment relative to the syringe body (34), so that the needle cannot be re-inserted by another attempted insertion of the plunger tip—and also to provide an even more robust harpoon-style coupling between the proximal portion of the needle (60) and the plunger tip (36). FIG. 17, which is similar to FIG. 13, features the addition of such misalignment of the needle member upon full withdrawal of the needle member into the syringe body using the twin coupling member (222) to prevent re-insertion of the needle member relative to the syringe body (i.e., to prevent re-use, or accidental/undesired contact of a needle tip with a person or object).

Figure 18A:
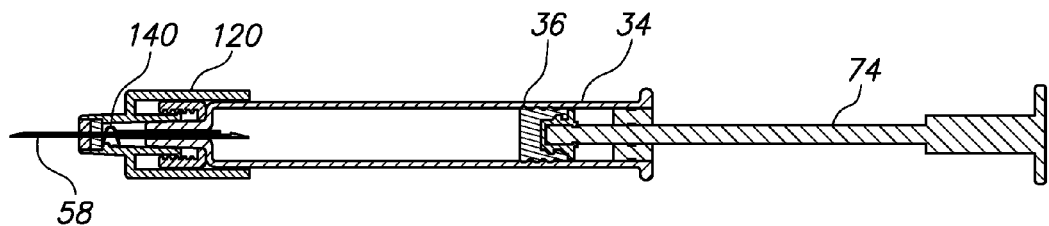
FIGS. 18A-18I illustrate various aspects of a safety syringe configuration in accordance with the present invention.
Figure 18B:
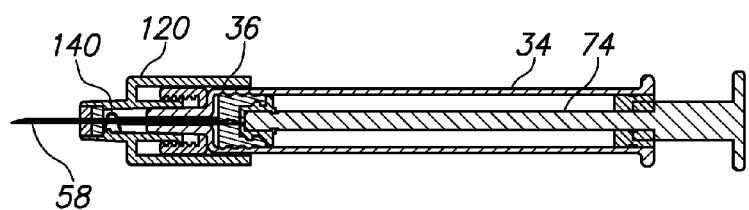
Figure 18C:
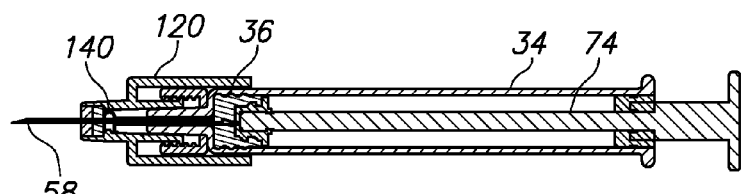
Figure 18D:
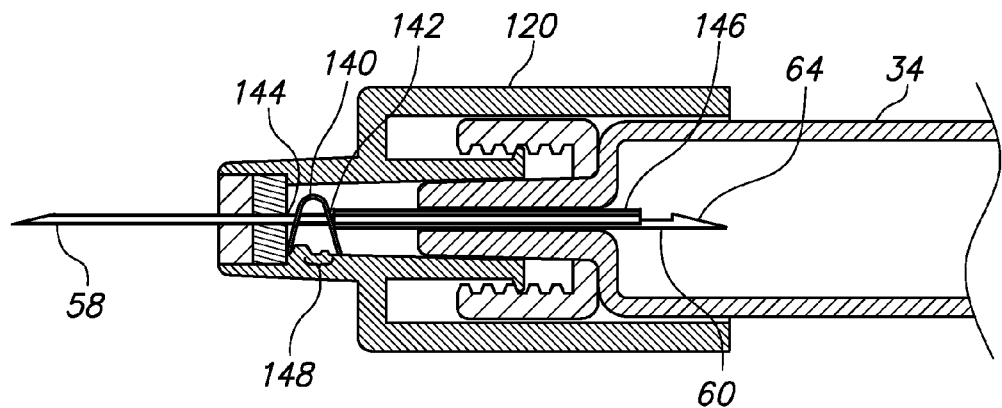
Figure 18E:
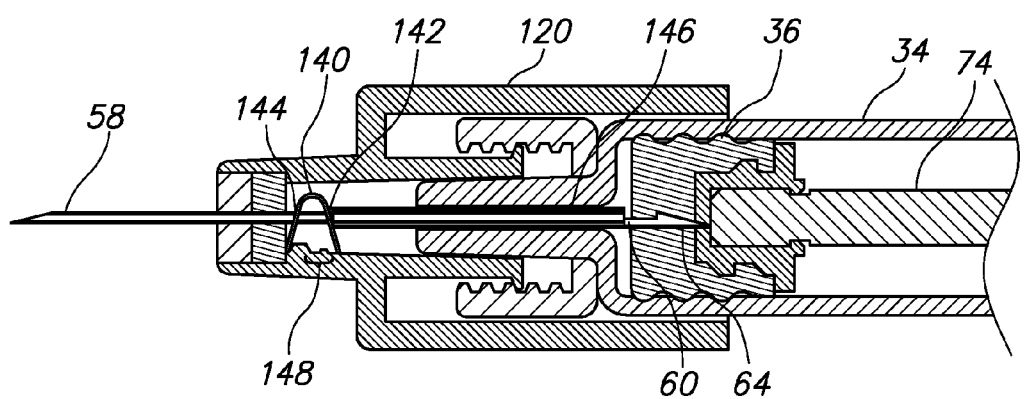
Figure 18F:
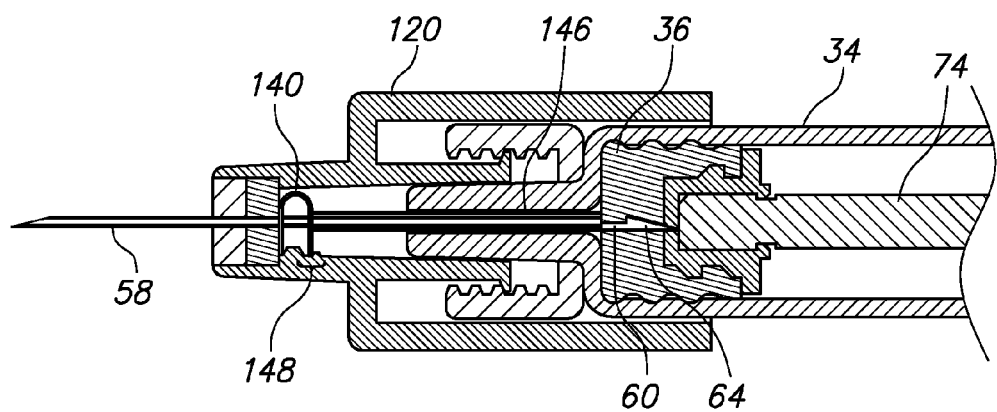
Figure 18G:
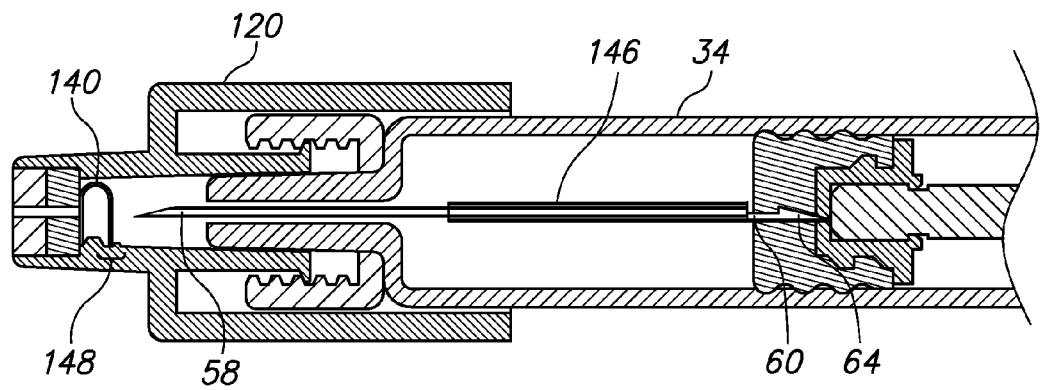
Figure 18H:
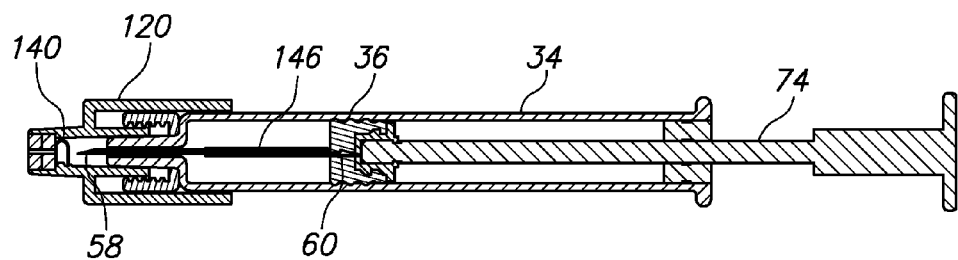
Figure 18I:
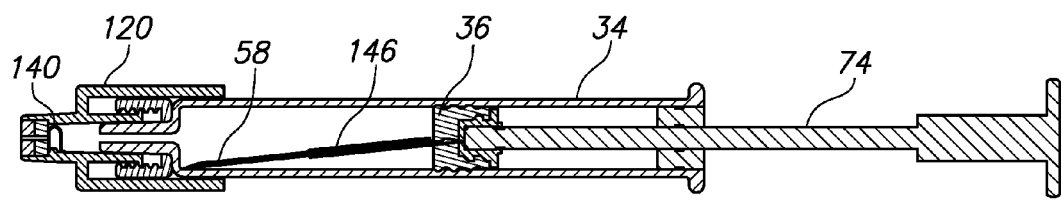
Figure 19:
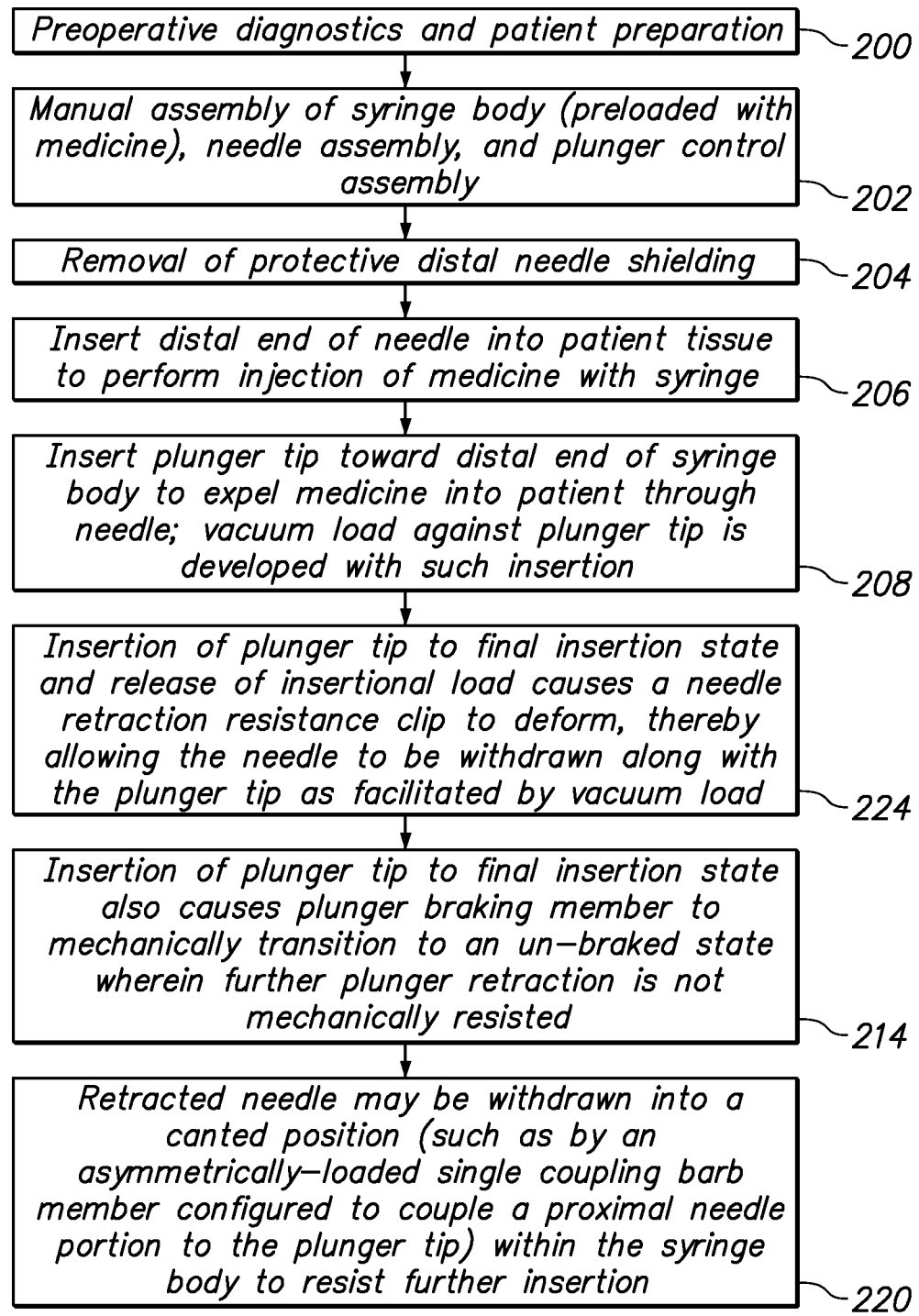
FIG. 19 illustrates a process for conducting an injection procedure utilizing a safety syringe configuration such as that described in reference to FIGS. 18A-18I.

Referring to FIGS. 18A-18I, an embodiment similar to that of FIGS. 12A-12G is illustrated, with the exception that the embodiment of FIGS. 18A-18I features a quite different mechanism for allowing insertion of the needle and resisting retraction until full insertion of the needle, after which retraction of the needle is facilitated by deformation of a clip member (140). For example, referring to the close-up views of FIGS. 18D and 18E, in FIG. 18D, a close-up view of the configuration of FIG. 18A, the clip member (140), with two through-apertures (142, 144) that are slightly out of alignment, prevents movement of the needle (58) relative to the syringe body (34). FIG. 18E shows the plunger tip almost fully, but not fully, inserted relative to the syringe body, as in FIG. 18B. Upon full insertion of the plunger tip (36), as in FIGS. 18C and 18F, a needle sleeve member, or a step formed in the outer geometry of the needle, compresses the clip member (140), causing the apertures (142, 144) to become more aligned, if not completely aligned, after which they may be held in such configuration by a feature (148) formed into the needle housing (120) configured to retain such configuration so that the needle may be withdrawn, such as by a manually applied load or vacuum load, as described above. In other words, the clip member (140) may be squeezed by virtue of a physical coupling through the needle assembly to the plunger tip (36), causing deformation (which may be configured to be plastic deformation or elastic deformation, depending upon the materials and dimensions selected for the clip; in an elastic deformation configuration, the holding feature 148 assists more prominently in retaining the deformed shape of the clip) of the clip (140) to a shape such as that shown in FIG. 18F, wherein the needle (58) is allowed to retract without substantial resistance from the clip, due to alignment of the apertures of the clip. FIG. 18H shows an incomplete withdrawal of the needle into the syringe body; FIG. 18I shows a complete withdrawal of the needle into the syringe body, with canting of the withdrawn needle to the side to prevent further insertion of the needle relative to the syringe body, as described above. The embodiment of FIG. 19 is similar to that of FIG. 15, with the exception that the embodiment of FIG. 19 features deformation of a needle retraction resistance clip, thereby allowing the needle to be withdrawn (224).

Figure 20A:
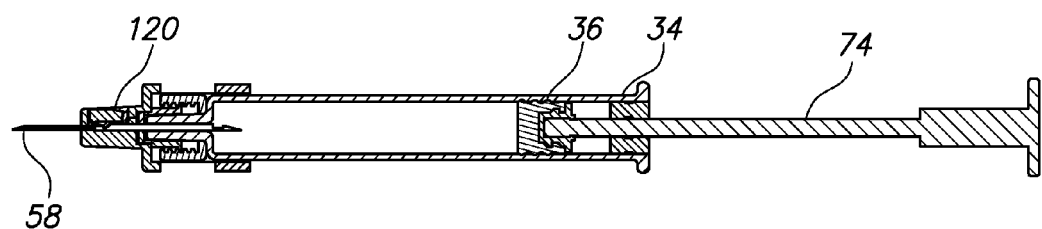
FIGS. 20A-20I illustrate various aspects of a safety syringe configuration in accordance with the present invention.
Figure 20B:
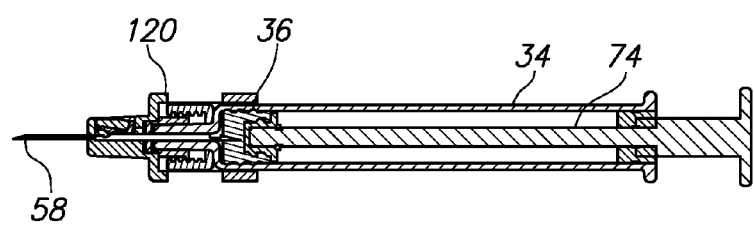
Figure 20C:
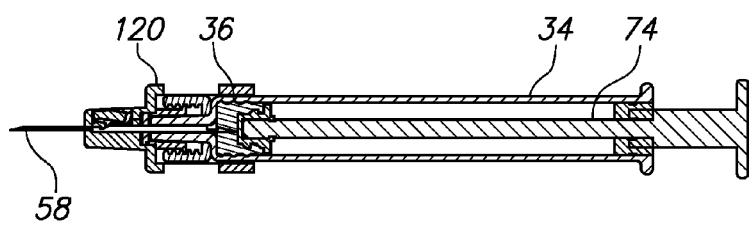
Figure 20D:
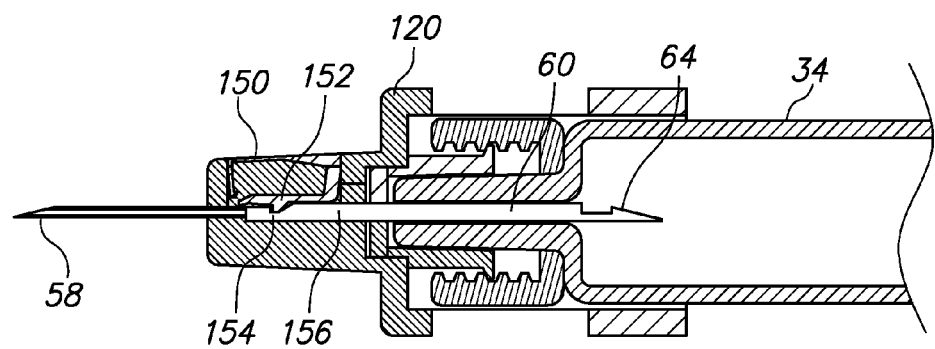
Figure 20E:
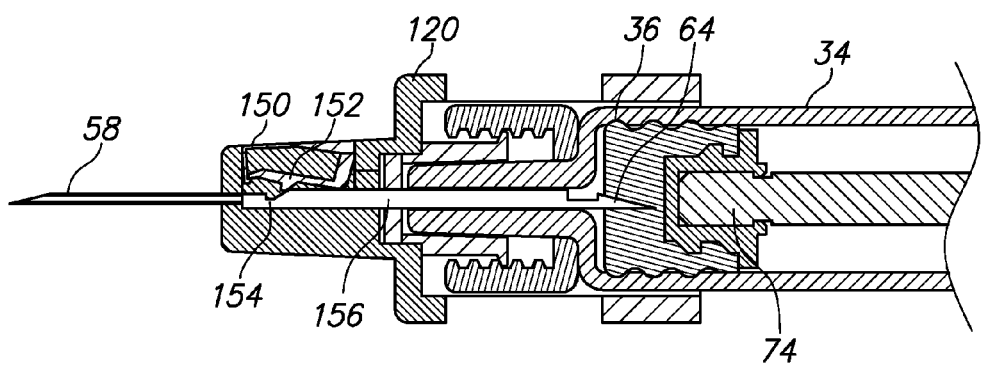
Figure 20F:
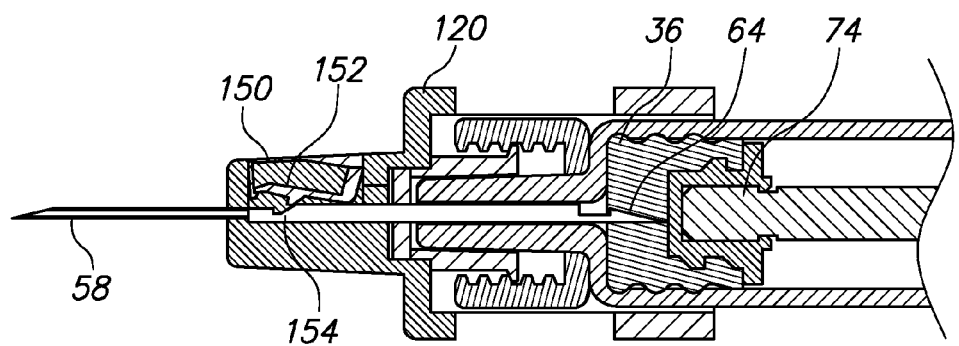
Figure 20G:
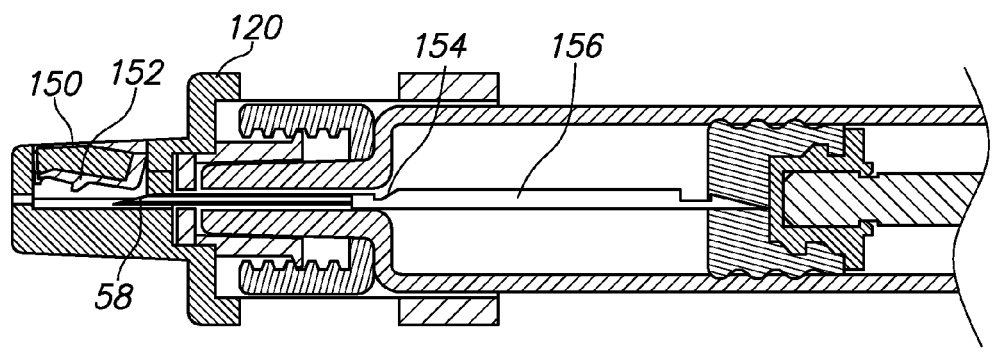
Figure 20H:
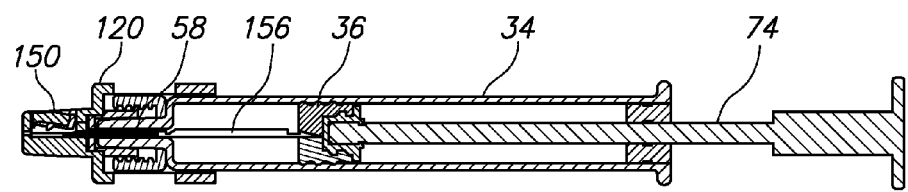
Figure 20I:
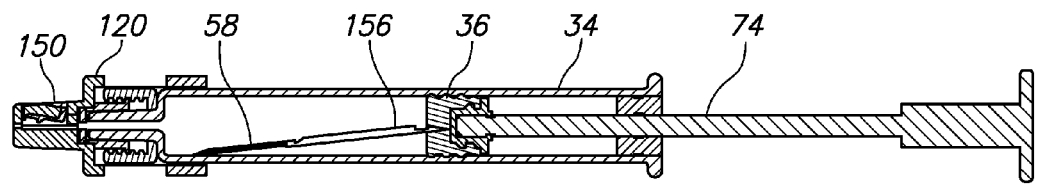
Figure 21:
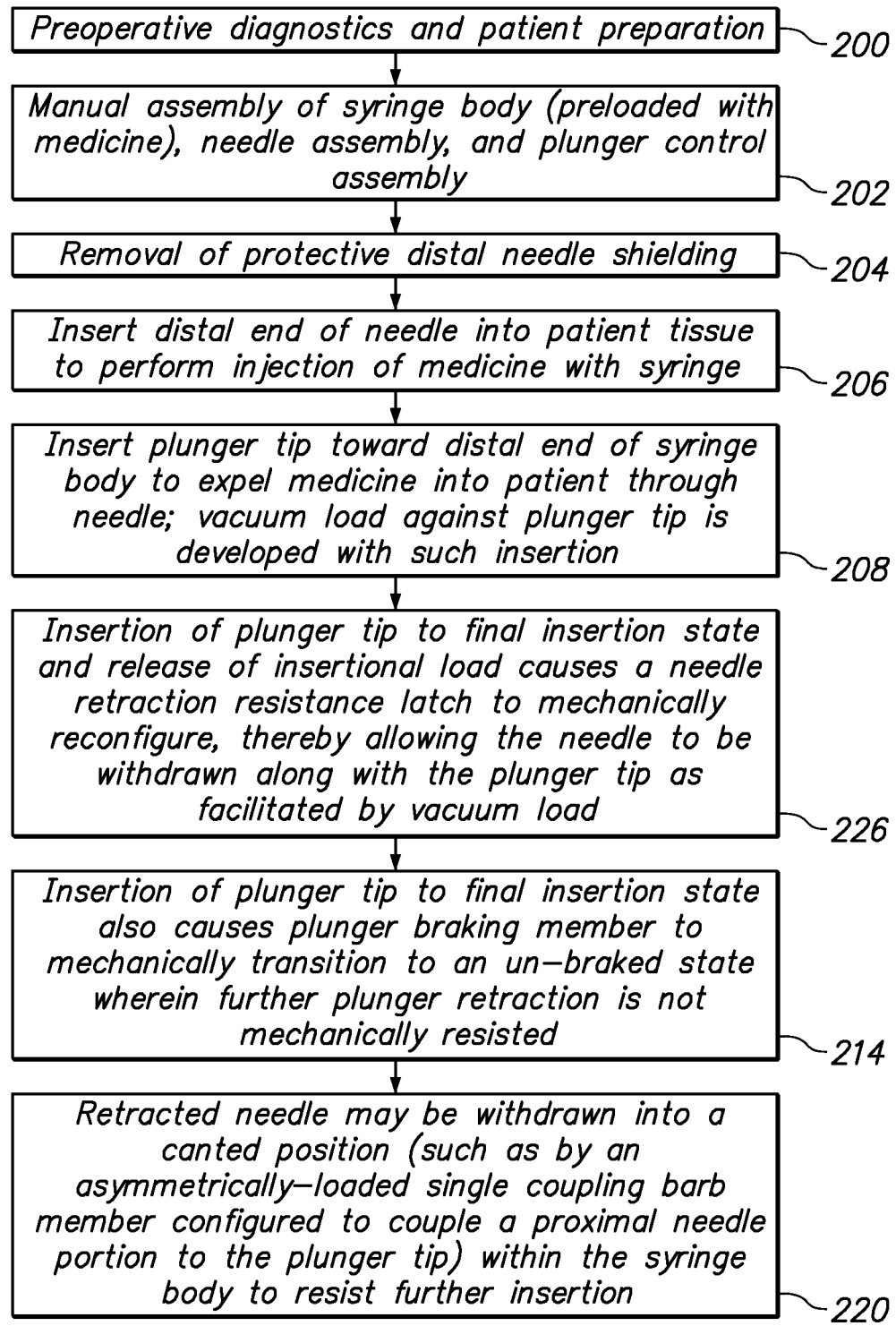
FIG. 21 illustrates a process for conducting an injection procedure utilizing a safety syringe configuration such as that described in reference to FIGS. 20A-20I.

Referring to FIGS. 20A-20I, an embodiment similar to that of FIGS. 12A-12G is illustrated, with the exception that the embodiment of FIGS. 20A-20I features a quite different mechanism for resisting needle retraction until full insertion of the needle, after which retraction of the needle is facilitated by movement of a cantilevered latch member (152) of a latch assembly (150) coupled to the distal needle housing (120). For example, referring to the close-up views of FIGS. 20D and 20E, in FIG. 20D, a close-up view of the configuration of FIG. 20A, the latch member (152) prevents withdrawal of the of the needle (58) relative to the syringe body (34) by interfacing with a recess (154) formed into the needle or a sleeve member coupled thereto. FIG. 20E shows the plunger tip almost fully, but not fully, inserted relative to the syringe body, as in FIG. 20B. Upon full insertion of the plunger tip (36), as in FIGS. 20C and 20F, the needle and/or needle sleeve (156) member is advanced slightly forward, dislodging the latch member (152) from the recess (154), after which the needle may be withdrawn (such as is shown in FIG. 20G), such as by a manually applied load or vacuum load, as described above. FIG. 20H shows an incomplete withdrawal of the needle into the syringe body; FIG. 20I shows a complete withdrawal of the needle into the syringe body, with canting of the withdrawn needle to the side to prevent further insertion of the needle relative to the syringe body, as described above. The embodiment of FIG. 21 is similar to that of FIG. 19, with the exception that the embodiment of FIG. 21 features mechanical reconfiguration of a needle retraction resistance latch, thereby allowing the needle to be withdrawn (226).

Figure 22A:
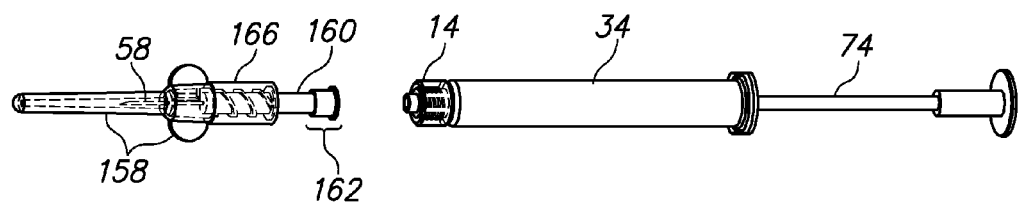
FIGS. 22A-22K illustrate various aspects of a safety syringe configuration in accordance with the present invention.
Figure 22B:
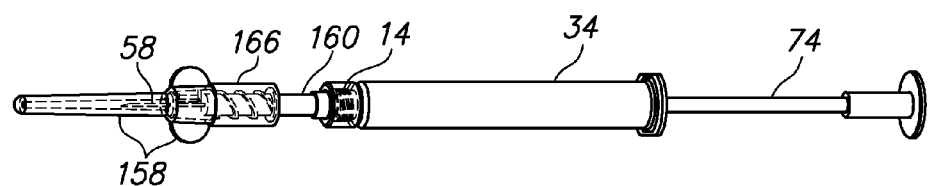
Figure 22C:
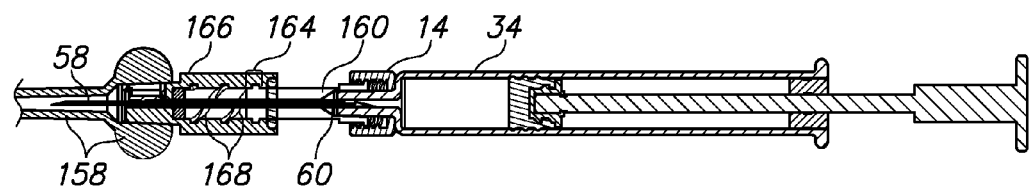
Figure 22D:
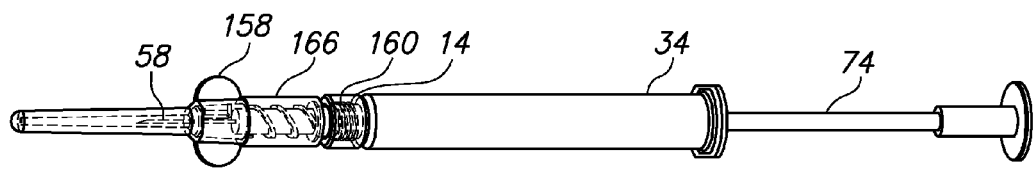
Figure 22E:
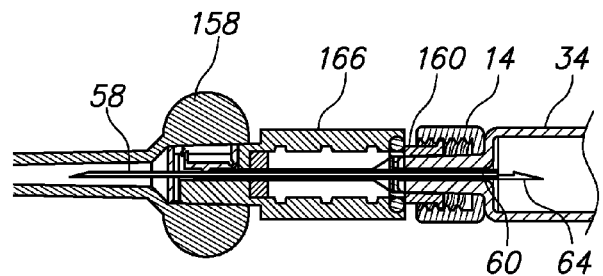
Figure 22F:
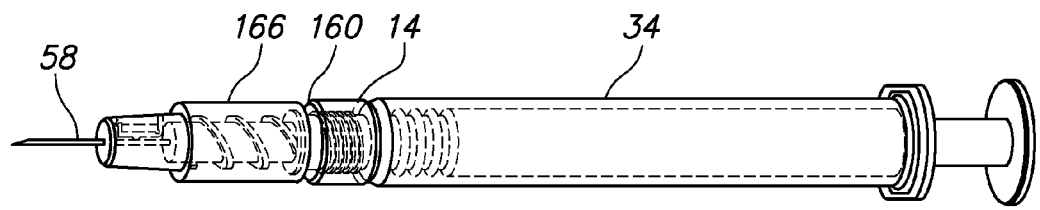
Figure 22G:
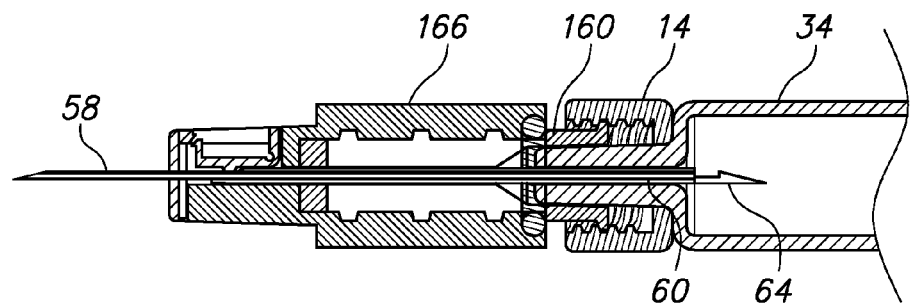
Figure 22H:
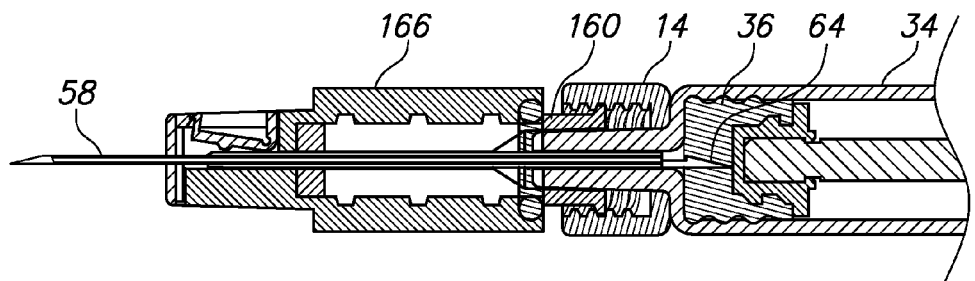
Figure 22I:
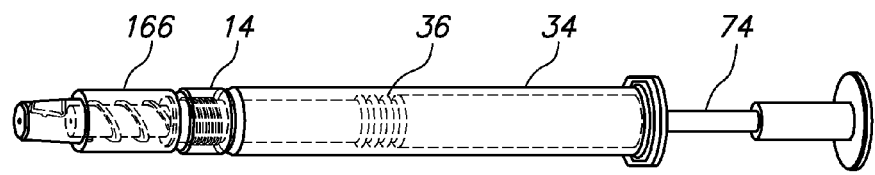
Figure 22J:
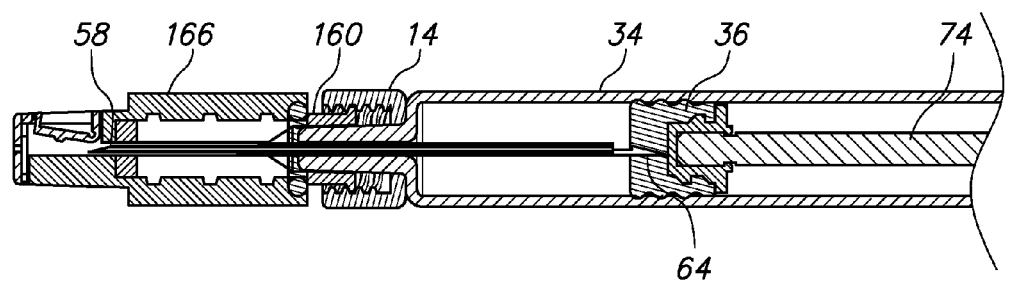
Figure 22K:
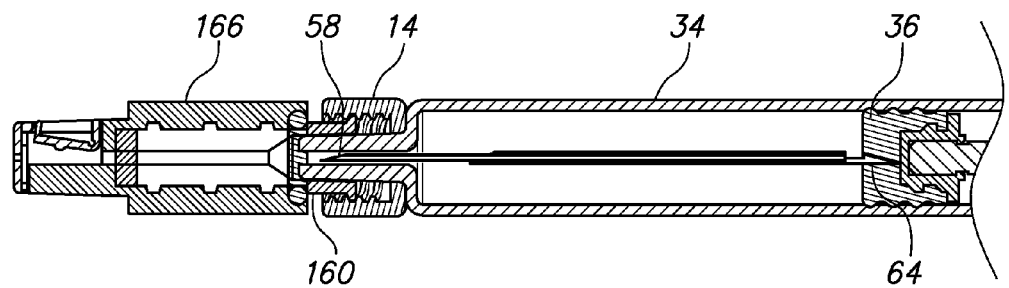

Referring to FIGS. 22A-22K, an embodiment is depicted wherein a needle assembly features a proximally disposed intercoupling member (160) configured to be coupled (via relative rotation) to a distal Luer fitting (14) of a conventional syringe assembly, and also configured to be coupled (also via relative rotation—preferably the same rotational direction as the first rotation) to an inner surface of the needle housing (166) in a manner wherein the proximal aspect (60, 64) of the needle remain shielded from the hands of an operator, or from other objects. Referring to FIG. 22A, the needle assembly comprises a needle coupled through a needle housing (166) and intercoupled intercoupling member (160) so that the proximal end of the needle (60, 64) does not extend beyond the proximal end of the intercoupling member (160). A removable needle shield (158) isolates the distal portion (58) of the needle and is removable at injection time; further, the removable needle shield (158) features rotational manipulation features, such as small wing features, to facilitate easy rotation of the needle assembly relative to the syringe body (34) to which it is to be coupled. Such features may be particularly useful for the home healthcare market wherein patients suffering from maladies such as arthritis may desire to use syringes for injection and have difficulty without physical feature aids. Referring to FIG. 22B, the syringe assembly and needle assembly are placed into contact with the Luer interface of the intercoupling member (160) positioned against the Luer interface of the syringe assembly. With twisting engagement, the intercoupling begins via the intercoupling member (160), as shown in the cross sectional view of FIG. 22C. With further twisting, the proximal coupling interface (164) of the intercoupling member (160) causes closer engagement of the intercoupling member (160) using the inner helical thread interface (168) of the needle housing—until the coupling is complete, as shown in FIGS. 22D and 22E. Subsequently the removable needle shield (158) may be removed and an injection of fluid started, as shown in FIGS. 22F and 22G. Upon full insertion of the plunger tip (36) relative to the syringe body (34), the proximal needle harpooning interface (64) may be coupled to the plunger tip (36), and an unlatching configuration similar to that shown in reference to FIGS. 20A-20I may allow for proximal withdrawal of the needle, as shown in FIGS. 22I-22K.

Figure 23:
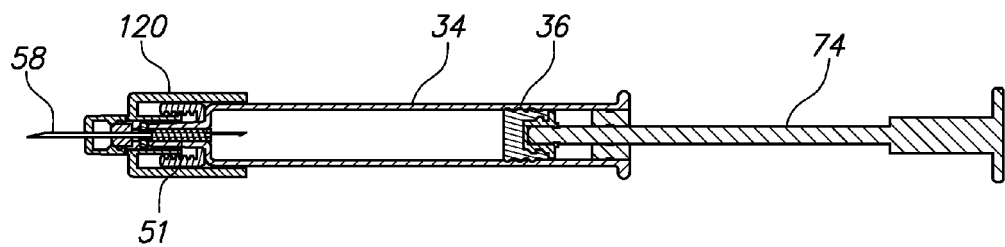
FIG. 23 illustrates various aspects of a safety syringe configuration in accordance with the present invention.

Referring to FIG. 23, a configuration similar to that depicted in FIG. 12A is illustrated, with exception that the configuration of FIG. 23 features an integrated spring member (51) intercoupled between the needle member (58) and the distal end of the syringe body (34) to provide a needle retraction load sufficient to retract the needle, as described above—but in the context of a vacuum retraction load.

Figure 24:
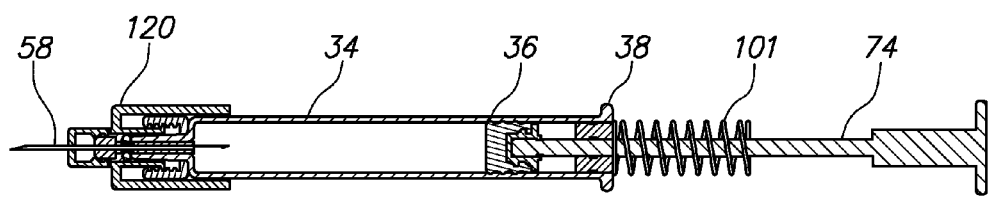
FIG. 24 illustrates various aspects of a safety syringe configuration in accordance with the present invention.

Referring to FIG. 24, a configuration similar to that depicted in FIG. 12A is illustrated, with exception that the configuration of FIG. 23 features an integrated spring member (101) intercoupled between the proximal end (38) of the syringe body (34) and the proximal end of the plunger insertion member (74) to provide a needle retraction load sufficient to retract the needle, as described above—but in the context of a vacuum retraction load.

FIGS. 23 and 24 illustrate that loads other than vacuum loads may be utilized to assist in retracting a needle member with various safety configurations described herein. Indeed, in simplified configurations, which may be desirable from cost and other perspectives, needle re-insertion prevention may be accomplished using needle assemblies such as those described herein, with only manual retraction of the needle member (i.e., while various self-retracting-after-full-insertion configurations are described herein, manual retraction configurations also may benefit from the safety provided by the needle assemblies described herein wherein re-insertion of a needle after a first full insertion is physically prevented).

Referring back to FIGS. 11, 13, 15, 19, and 21, the syringe body (preloaded with medicine), needle assembly, and plunger control assembly are illustrated (202) as being part of an in-situ process (i.e., adjacent the point of use—such as in a hospital or home healthcare scenario, and after preoperative diagnostics and patient preparation 200). In other embodiments, a plunger control assembly such as that illustrated in FIGS. 6 and 7B (44) may arrive at the intervention site pre-assembled with a syringe body (i.e., such an assembly would be pre-assembled before delivery to the intervention site); further, in other embodiments, a needle assembly such as that illustrated in FIGS. 6 and 7A (32) may arrive at the intervention site pre-assembled with a syringe body (i.e., such an assembly would be pre-assembled before delivery to the intervention site); indeed, in other embodiments, both a needle assembly (32) and plunger control assembly (44) may be pre-assembled with a syringe body at the preparation factory or other location before delivery to the intervention site.

Suitable polymeric materials for the various components of these embodiments include but are not limited to acetal, polycarbonate, poly vinyl chloride, polypropylene, polystyrene, ABS, nylon, glass-filled nylon, glass-filled acetal, peek, glass-filled peek, carbon-fiber-filled peek, COC (cyclic olefin copolymer), COP (cyclic olefin polymer), PEI (Ultem), glass-filled PEI, and pekk, as well as copolymers thereof.

Suitable structural metals for structures such as the plunger insertion member include but are not limited to stainless steel, steel with chrome coating, brass, nickel, and titanium, as well as alloys thereof.

Suitable needle member sizes range from about 34 gauge/6 millimeters long—to about 20 gauge/2.5 inches long.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit and scope of the invention. In addition, many modifications may be made to adapt a particular situation, material, composition of matter, process, process act(s) or step(s) to the objective(s), spirit or scope of the present invention. Further, as will be appreciated by those with skill in the art that each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the devices described for carrying out the subject diagnostic or interventional procedures may be provided in packaged combination for use in executing such interventions. These supply "kits" may further include instructions for use and be packaged in sterile trays or containers as commonly employed for such purposes.

The invention includes methods that may be performed using the subject devices. The methods may comprise the act of providing such a suitable device. Such provision may be performed by the end user. In other words, the "providing" act merely requires the end user obtain, access, approach, position, set-up, activate, power-up or otherwise act to provide the requisite device in the subject method. Methods recited herein may be carried out in any order of the recited events which is logically possible, as well as in the recited order of events.

Exemplary aspects of the invention, together with details regarding material selection and manufacture have been set forth above. As for other details of the present invention, these may be appreciated in connection with the above-referenced patents and publications as well as generally known or appreciated by those with skill in the art. For example, one with skill in the art will appreciate that one or more lubricious coatings (e.g., hydrophilic polymers such as polyvinylpyrrolidone-based compositions, fluoropolymers such as tetrafluoroethylene, hydrophilic gel or silicones) may be used in connection with various portions of the devices, such as relatively large interfacial surfaces of movably coupled parts, if desired, for example, to facilitate low friction manipulation or advancement of such objects relative to other portions of the instrumentation or nearby tissue structures. The same may hold true with respect to method-based aspects of the invention in terms of additional acts as commonly or logically employed.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless the specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims, or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

The invention claimed is:

1. A safety syringe system, comprising:
 a syringe body forming a fluid reservoir and having proximal and distal ends;
 a plunger tip positioned within the fluid reservoir in a configuration such that medicinal fluid may be contained within the fluid reservoir;
 a needle assembly removably coupleable to the distal end of the syringe body such that the medicinal fluid may be transferred through a retractable needle coupled to a needle housing comprising the needle assembly upon insertion of the plunger tip relative to the syringe body, wherein the needle assembly comprises a movable needle insertion-preventing member;
 a plunger control assembly coupled to the plunger tip and configured to facilitate manual insertion of the plunger tip relative to the syringe body, wherein upon insertion of the plunger tip to a final insertion state and release of an associated manual insertion load, a retraction load coupled between the syringe body and the plunger tip causes the plunger tip to be proximally withdrawn, pulling the retractable needle proximally relative to the needle housing to a retracted state wherein a distal tip of the needle becomes mechanically locked into an encapsulated configuration wherein it is no longer exposed for injection; and
 a releasing member operatively coupled to the needle insertion-preventing member, wherein the releasing member comprises a push member configured to be compressively loaded when the plunger tip is urged into the final insertion state,
 wherein the needle insertion-preventing member is configured to prevent re-insertion of the needle relative to the syringe body after the needle has been placed in the retracted state,
 wherein the releasing member is configured to remove a fixing constraint from the insertion-preventing member when the plunger tip reaches the final insertion state, and
 wherein the push member is configured to release a mechanical latch configured to hold the needle fixed in place relative to the syringe body, thereby releasing the needle such that it may be proximally withdrawn into the retracted state.

2. The system of claim 1, wherein the fluid reservoir comprises a substantially cylindrical volume.

3. The system of claim 1, wherein the syringe body comprises a glass material.

4. The system of claim 1, wherein the syringe body comprises a polymeric material.

5. The system of claim 1, wherein the plunger tip comprises an elastomeric material.

6. The system of claim 5, wherein the elastomeric material comprises a butyl-based rubber.

7. The system of claim 1, wherein the needle is a hypodermic needle.

8. The system of claim 7, wherein the hypodermic needle is a standard size between about 20 gauge and about 34 gauge.

9. The system of claim 1, wherein the insertion-preventing member is configured to move along an axis that is substantially perpendicular to a longitudinal axis of the needle.

10. The system of claim 1, wherein the mechanical latch is configured to interface directly with the needle.

11. The system of claim 1, wherein the mechanical latch is configured to interface with a needle interfacing member that is interfaced directly with the needle.

12. The system of claim 11, wherein the needle interfacing member comprises a compliant O-ring.

13. The system of claim 1, wherein the plunger control assembly comprises a plunger tip coupler member configured to be intercoupled with the plunger tip.

14. The system of claim 13, wherein the plunger tip coupler comprises one or more helical threads configured to be inserted relative to the plunger tip to couple the plunger tip coupler to the plunger tip.

15. The system of claim 13, wherein the plunger tip coupler is fixedly coupled to a plunger insertion member having a proximal end configured to be manually manipulated.

16. The system of claim 15, further comprising a plunger guiding flange through which the plunger insertion member is inserted, the plunger guiding flange being removably coupleable to the proximal end of the syringe body.

17. The system of claim 16, wherein a brake assembly is intercoupled between the plunger guiding flange and the plunger insertion member, the brake assembly being configured to prevent retraction of the plunger insertion member until after the first time it has been inserted to place the plunger tip in the final insertion state.

18. The system of claim 17, wherein the brake is configured to reside in a braked state relative to the plunger guiding flange until the plunger insertion member is utilized to place the plunger tip in the final insertion state, after which the brake is configured to mechanically transition to an unbraked state relative to the plunger guiding flange wherein it is configured to allow the plunger insertion member to be retracted away from the syringe body.

19. The system of claim 1, wherein the retraction load is developed by an integrated spring member.

* * * * *